United States Patent [19]

Saffran

[11] Patent Number: 5,653,760
[45] Date of Patent: *Aug. 5, 1997

[54] METHOD AND APPARATUS FOR MANAGING MACROMOLECULAR DISTRIBUTION

[76] Inventor: Bruce N. Saffran, 1527 Beacon St. #4, Brookline, Mass. 02146

[*] Notice: The term of this patent shall not extend beyond the expiration date of Pat. No. 5,466,262.

[21] Appl. No.: 513,092

[22] Filed: Aug. 9, 1995

Related U.S. Application Data

[63] Continuation-in-part of Ser. No. 114,745, Aug. 30, 1993, Pat. No. 5,466,262.

[51] Int. Cl.[6] .................................................. A61F 2/02
[52] U.S. Cl. .......................... 623/11; 623/1; 623/16; 606/74; 606/86; 606/154
[58] Field of Search .............................. 623/11, 16, 1; 606/74, 86, 154

[56] References Cited

U.S. PATENT DOCUMENTS

| | | | |
|---|---|---|---|
| 4,206,516 | 6/1980 | Pilliar | 3/1.9 |
| 4,321,711 | 3/1982 | Mano | 3/1.4 |
| 4,642,120 | 2/1987 | Nevo-Sui . | |
| 4,693,720 | 9/1987 | Schamberg . | |
| 4,801,299 | 1/1989 | Brendel et al. | 623/1 |
| 4,859,383 | 8/1989 | Dillon | 264/43 |
| 4,911,717 | 3/1990 | Gaskill, III | 623/11 |
| 5,002,583 | 3/1991 | Pitaru-Sandu . | |
| 5,084,051 | 1/1992 | Tormala . | |
| 5,152,782 | 10/1992 | Kowligi . | |
| 5,383,928 | 1/1995 | Scott . | |
| 5,397,353 | 3/1995 | Oliver et al. | 623/11 |

*Primary Examiner*—John G. Weiss
*Assistant Examiner*—Francis K. Cuddihy

[57] ABSTRACT

This invention is designed to help restrain small structural or minor fracture fragments (5), and the macromolecules they produce (8) in specified compartment. The device is composed of a single sheet of material (1) that in its principal embodiment is supplied as a thin, pliable, fabric that is flexible in three dimensions and is minimally porous to macromolecules. When the method of use contains the secondary step of affixing a treating material (12) to the device prior to use, additional materials can be delivered directly and preferentially into specific compartments. Moreover, because the device can be made of a soft fabric, a needle can be passed through the device and additional treating materials can be repeatedly injected into and contained after the device has been deployed. The invention also permits delivery of energy (23) directly and specifically to the treated surface. The rate of repair can be further accelerated by the attachment of a treating material (12), either mechanically or by chemical bond (24), to one surface of the device.

18 Claims, 30 Drawing Sheets

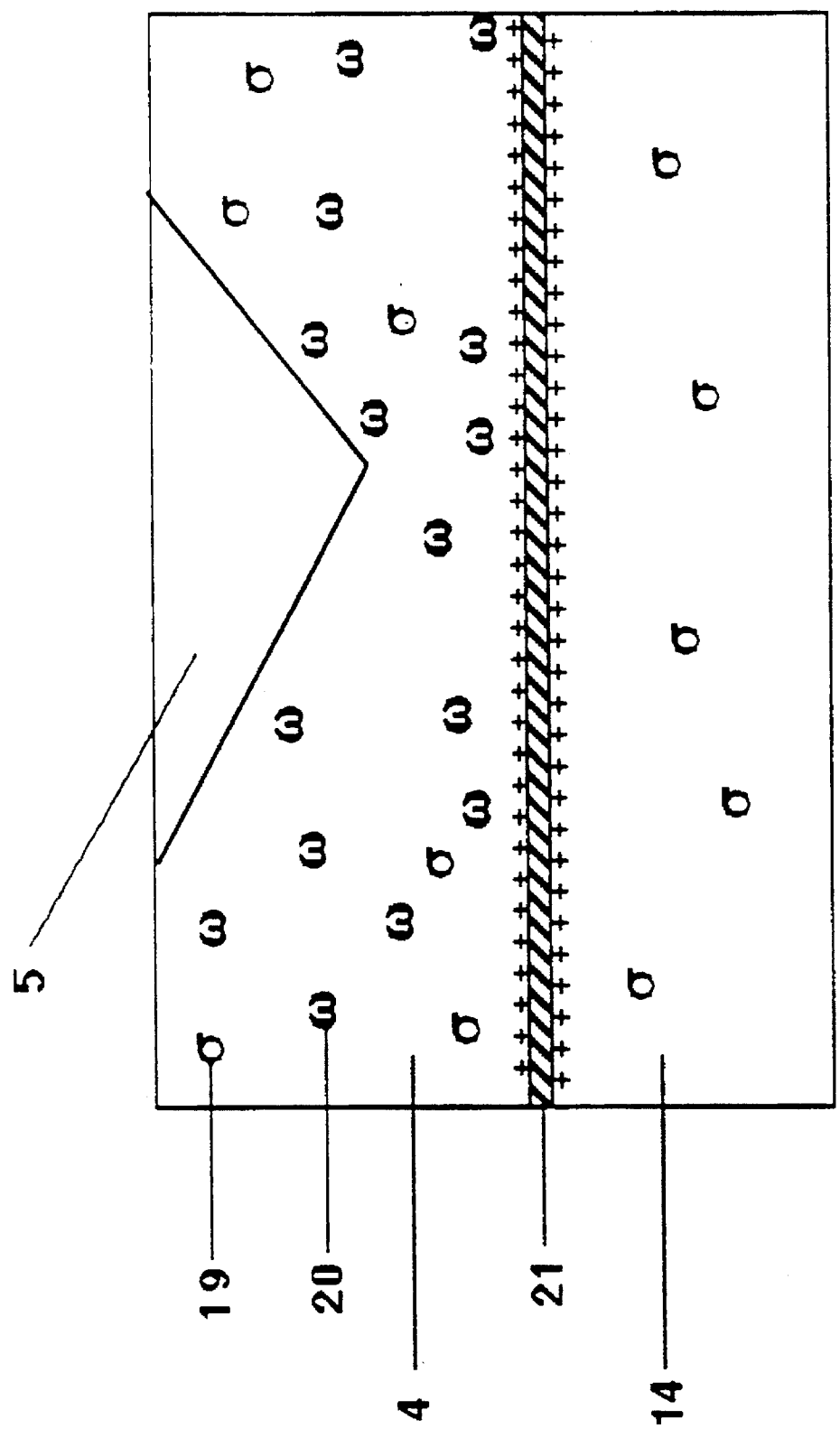

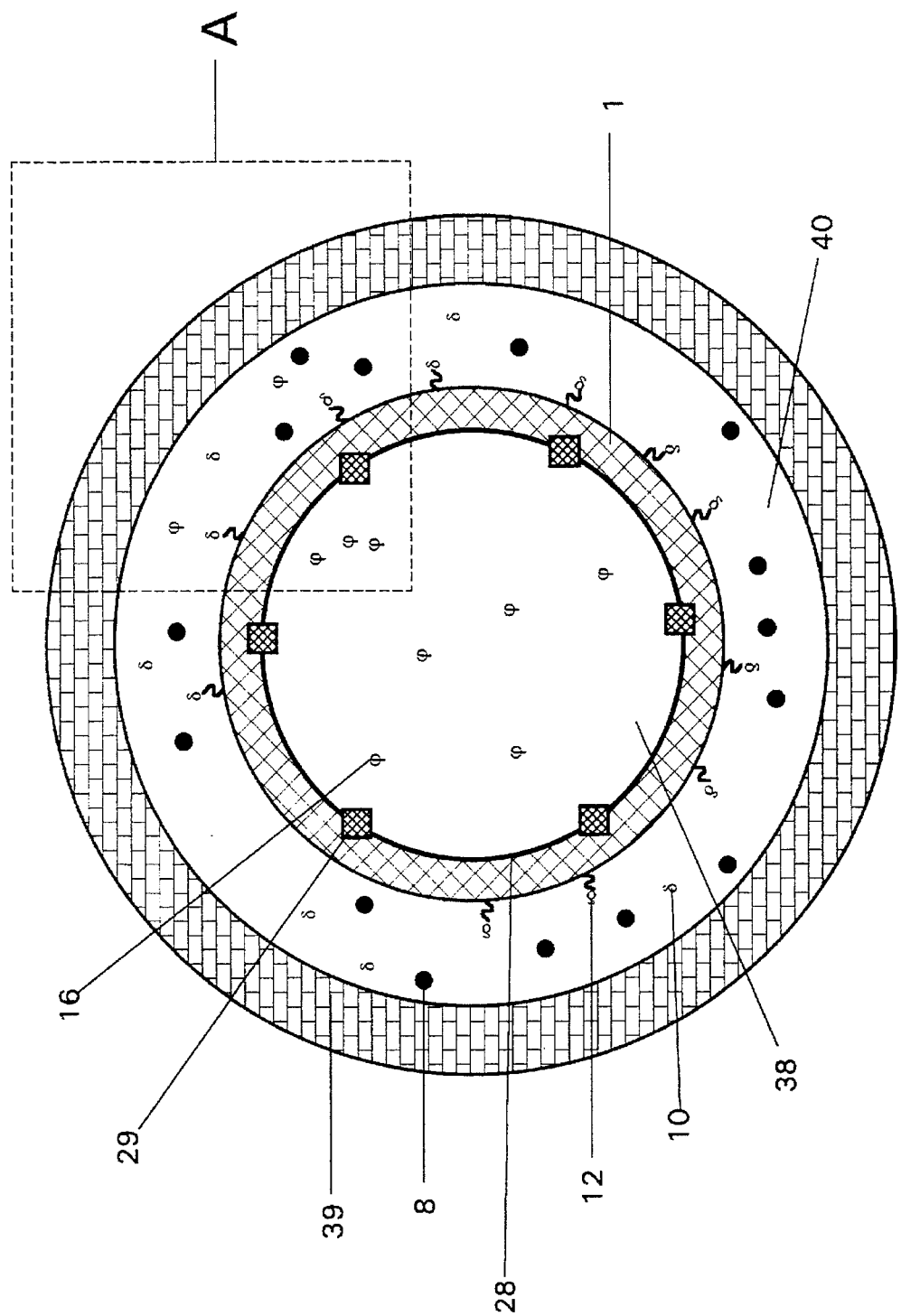

METHOD AND APPARATUS FOR MANAGING MACROMOLECULAR DISTRIBUTION

CROSS REFERENCES TO RELATED APPLICATIONS

This application is a Continuation-In-Part of U.S. application Ser. No. 08/114,745 filed Aug. 30, 1993 for a Malleable Fracture Stabilization Device with Micropores for Directed Drug Delivery (U.S. Pat. No. 5,466,262, Issue date Nov. 14, 1995).

A divisional application of my U.S. patent for a Malleable Fracture Stabilization Device with Micropores for Directed Drug Delivery (U.S. Pat. No. 5,466,262, Issue date Nov. 14, 1995), is pending (Appl. 08/557,432, Filing date Nov. 13, 1995).

BACKGROUND OF THE INVENTION

1. Field of Invention

This invention relates to the treatment of injured tissues within human or animal bodies, specifically to the way injured tissues are joined and the way macromolecules are directed to promote healing. The invention can be modified such that a treating material, when affixed to a major surface of the minimally-porous sheet, can be directed preferentially to the site of injury. Although I will frame this invention initially in terms of treatment of traumatic injuries, I will also discuss this invention in the treatment of many other conditions including treatment of metastases, infections, metabolic conditions such as osteoporosis, primary neoplasms, and vascular disease.

2. Description of Prior Art

Traumatic injury remains the single most important contributor to long-term disability among working-aged persons. Because the costs of rehabilitation and the loss of productivity during recovery are great, additional ways to decrease "down time" following injury are continually being sought. Although many tissues are commonly fractured in traumatic injury, e.g., the liver, the kidney, the bowel, the bladder, the spleen and the testicle, perhaps the most often-injured tissues are the bones.

Currently used techniques of bone fracture fixation:

When tissue is injured, a surgeon must first decide whether the patient needs an operation to fix the injury. Closed reduction refers to a non-operative method of fracture fixation whereby a surgeon manipulates the fractured internal structures into anatomic alignment from outside the body. Many simple bone fractures are treated in this way. After closed reduction, the surgeon casts the extremity, and the bone is left to heal. Serious bone fractures cannot be treated by closed reduction. These fractures either involve shattered bone (comminuted fractures), or involve bones critical to support of the axial skeleton such as the spine, pelvis, and/or the femur. These bones usually will not heal unless they are fixed in position in the operating room using the technique of internal fixation. Since this invention deals with a method of internal fixation, I will discuss internal fixation with respect to treating bone fractures in more detail.

Internal fixation of bone fractures, as it is currently practiced, involves exposing the fracture and affixing a rigid stabilization device to the bone. The current state of the art is to approximate the fragments and then bridge the site of injury with a rigid rod or plate such that force is transmitted across the device and not the small fragments. The hope is that new bone will form between the small fragments and ultimately bridge between the small fragments and the major fragments. If the major fragments do not join, it is termed "non union". A good result is when bony bridging occurs rapidly between large and small fracture fragments. Unfortunately good results are relatively rare and, in complicated bone fractures, reoperation and refixation are usually the rule. Fractures that require a second and sometimes third and fourth operation rarely heal well, and the patient is left with permanent deformity. Consequently, it is critically important to get the operation right the first time.

Complex fractures often heal with poor results:

The reasons complex bone fractures do not heal well are unknown; however several studies have shown that a cascade of both molecular and cellular events is initiated once tissue is injured, and that for some reason in severe injuries, this cascade is interrupted.

Following injury, specific proteins are made by injured cells and are secreted into the interfragmentary space. When an adequate concentration of these macromolecules is attained within the interfragmentary space, osteoblasts and fibroblasts are recruited and a "scaffolding" is constructed. If the concentration of these growth-promoting molecules within the interfragmentary space remains high enough, a cellular matrix is laid upon the scaffolding and, if the patient is lucky, the tissue is healed.

When the patient is not as lucky, the small bone fragments resorb, i.e., are biodegraded by host enzymes, leaving a gap between major fragments. Small bone fragments are naturally resorbed unless they are bathed in an adequate concentration of growth-promoting macromolecules. The patient subsequently has a defect between proximal and distal fracture segments. Surgical intervention is subsequently required for bone grafting to maintain limb length. If the limb-lengthening procedure fails, which is often the case, non-union results. Non-unions very rarely heal with an acceptable physiologic result and as a consequence, they are a very common reason for malpractice lawsuits. Not surprisingly, non-union is one of the most feared long-term complications in orthopedic surgery.

Often during bone fracture healing, bone growth factors produced by the injured cells diffuse into surrounding muscles. The efflux of growth-promoting proteins from the fracture site into the soft tissues is harmful for at least two reasons. First, there results a lower concentration of growth factors bathing the fracture fragments. Second, because bone growth factors stimulate bone growth, the diffusion of bone growth factors into surrounding muscles causes bone to be formed within them (heterotopic bone). Because, heterotopic bone can limit range of motion within that muscle for the life of the patient, it too is a major cause for clinical concern.

The problems of non-union and heterotopic bone formation have been recognized for well over a hundred years, and are now thought to be a result of two major factors. First, there becomes a paucity of growth-promoting molecules in the interfragmentary space during a critical stage of healing. Even well-aligned and well-approximated fragments resorb when there are insufficient growth-promoting macromolecules within the interfragmentary space. Second, the movement of small fragments out of the plane of the fracture increases the distance that must be bridged by new bone. Heterotopic bone is formed when these bone growth macromolecules diffuse into neighboring soft tissues. Orthopedic surgeons have tried to prevent non-union and heterotopic bone formation in a number of ways, and the most significant and relevant of these will be discussed below.

Compression plate fixation:

The simplest internal fixation device currently in use is the compression plate. Compression plate fixation involves bridging the fracture with a rigid bar of metal that has been fixed to the major fragments. Although adequate for simple transverse fractures, a plate is unable to secure shattered bone because fragments are often small size and "free-floating" within the fracture cavity. Furthermore, compression plates are unable to contain the macromolecules produced by the fracture fragments. Rigid plates, since they are not flexible in three dimensions, cannot cover a fracture in a continuous fashion even if they are laid close together. Consequently, growth-promoting macromolecules and small fragments can diffuse around them and into the surrounding soft tissues.

Moreover, compression plates remove virtually all stress at the sites they are affixed such that the hardest bone, i.e., the cortex, becomes "spongified" increasing the risk of refracture. This effect is most pronounced the longer the plate is in place. One of the reasons that spongification is thought to occur is that the compression plate is unable to restrain a high enough concentration of bone growth factors at the plate-bone interface.

Intramedullary rod fixation:

Another common method used to fix complex long bone fractures is using an intramedullary (IM) rod. IM rod fixation involves pounding a rigid bar down the medullary cavity such that it bridges the fracture. Although IM rod fixation has the benefit of not having to expose the fracture site itself, the process of IM rod insertion is very traumatic to the bone. IM rods displace small fragments and disrupt the medullary blood supply; and because there is no mechanism to restrain either small fragments or macromolecules produced by the fracture, small fragments are free to resorb. If the small fragments surrounding the rod resorb (which is common after IM rod fixation of comminuted fractures), the patient has a defect between proximal and distal fracture segments resulting in non union. Moreover, bony bridging sometimes occurs between healing bone and the IM rod itself, making rod removal difficult after healing has taken place. Occasionally the difficulty in removing the rod results in further damage to the healing bone or damage to adjacent soft tissues.

Recent developments in the art:

Several additions to the fracture treatment armamentarium have been introduced over the past few years which have attempted to address these problems. Unfortunately, each type also suffers from particular disadvantages when used in clinical practice.

1. Porous Substrates:

Recently, several authors have described using a porous substrate to provide a scaffold for bone ingrowth, e.g., Tormala et al., U.S. Pat. No. 5,084,051. These authors teach that porous, rigid ceramics can be used to serve as an anchor for growing cells. Although potentially useful to aid in cellular bridging across a fracture, their porosity precludes macromolecular restrainment. The critical feature of these devices is that they contain pores large enough to permit cells to grow into them. Since macromolecules are orders of magnitude smaller than cells, they are not restrained within the interfragmentary space by these devices. Consequently a major determinant of whether or not a fragment is resorbed, i.e., the interfragmentary concentration of growth factors and the like, is not addressed. Therefore, when devices such as those described by Tormala et al, are used, macromolecules produced by the fracture are free to exit the interfragmentary space and pass unhindered into the surrounding tissues.

Because they are designed to allow cellular ingrowth, these devices form an irreversible bond with the host tissue. Small fracture fragments are then free to resorb, causing native tissue to be replaced with prosthetic. Native tissue is always preferable to prosthetic, unless it is cancerous or is severely arthritic. Foreign material, no matter of what it is composed, dramatically increases the risk of infection by blood-borne bacteria. Orthopedic surgeons almost universally agree that the sooner all prostheses are removed, the better. Implantable prosthetics, however, remain in the body for life.

2. Bone chips or other forms of exogenous bone matrix:

Another recent development in the treatment of non-union fractures is the administration of bone chips or other forms of exogenous bone matrix. The idea is to provide a substrate for growing cells and incorporate the polymer when it becomes surrounded by growing bone. These devices, such as the implantable fixed prosthetic device (see U.S. Pat. No. 5,002,583 to Pitaru-Sandu, 1991), are composed of a rigid core surrounded by collagen that, once in the body also forms a biological bond with and integrates into host tissues. Although potentially suitable for affixing a prosthetic device to native bone, these devices are poorly suited for treatment of fractures for at least three reasons First, they are unable to restrain macromolecules produced by the fracture within the interfragmentary space. Second, the devices are rigid, making it impossible to modify them in the operating room to suit a specific need. Surgeons rarely know exactly the extent and dimensions of tissue injury until a fracture is exposed. Third, since these devices also form an irreversible bond with the host tissue, small fracture fragments resorb, causing native tissue to be replaced with prosthetic.

3. Implantable gels and injectable cements:

In the case of implantable gels or injectable cements, e.g., U.S. Pat. No. 4,642120 to Nevo-Svi, 1987, a gel is provided as an amorphous jelly containing biologically active molecules and/or living cells, or is supplied as a "quick drying bone cement". These devices are also not ideal for the treatment of comminuted fractures for several reasons, of which four deserve mention as they limit the use of these agents in clinical practice. First, because they are not supplied or applied as a sheet, the injected cement/gel/cells are free to float around the site of injury. Consequently, not only are the macromolecules critical to the healing process displaced by the gel and forced into the surrounding muscles, but over time, the injected material is also free to egress from the fracture site because there is no significant means to contain it at the site it was originally injected. Second, even if supplied as a paste, gels are unable to tightly bind small fragments together. Fragments are free to "float" around the cavity and out of the plane formed by the major fracture fragments. The failure to prevent small fragment resorption results in deformity and limb shortening if and when the fracture heals. Third, if the gel does harden within the interfragmentary space, native fracture fragments will be hindered in their ability to bridge among themselves by the intervening prosthetic. Thus, native fragments will be replaced by prosthetic as in the rigid prosthetic described above. Finally, cells and/or medications are free to diffuse from the gel in all directions, which can result in heterotopic bone formation. If a gel fragment lodges between muscle strands and forms bone around it, this could limit the use of that muscle forever.

4. Potential use of the flexible polymer coated sheet of Scharnberg et al. (U.S. Pat. No. 4,693,720)

Scharnberg et al. (U.S. Pat. No. 4,693,720) have disclosed a flexible polymer coated sheet, that is taught to be used to patch defects in the anterior abdominal wall following hernia surgery. Although this device could potentially be used to treat fractures, as claimed it does not have macromolecular restrainment means such that it can substantially restrain macromolecules produced by injured tissue within a particular space, e.g., "the interfragmentary space". Although these authors do teach of a flexible device, these authors fail to include the critical aspect of minimal-porosity. Consequently, the failure of their device to have "macromolecular restrainment means", would permit their device to allow growth factors and the like to diffuse out of the interfragmentary space and into the surrounding tissues.

5. Potential use of a non-porous graft such as that described by Kowligi et al (U.S. Pat. No. 5,152,782)

Since a major problem with healing comminuted fractures is that interfragmentary macromolecules leave the interfragmentary space, one might think that a non-porous graft could be used to restrain them and subsequently speed healing. Although this true to some extent, I have found unexpectedly that if small molecules such as water, urea, bicarbonate, and hydrogen ions are permitted to pass through the device, healing occurs much more quickly. For example, if hydrogen ions are not free to cross the device, the pH will fall within the interfragmentary space. If the pH falls, enzymes will be less active, and healing will be slower. Furthermore, if small metabolites are contained within the interfragmentary space, negative feedback loops will be activated thereby decreasing the rate of healing. Finally, the use of a non-porous graft will hinder the passage of desirable small molecules such as glucose and water into the interfragmentary space. Clearly, what is needed is a device that can restrain macromolecules but allow free passage of small molecules.

6. The Malleable Fracture Stabilization Device with Micropores for Directed Drug Delivery The applicant of the present invention, in U.S. patent application Ser. No. 08/114,745, filed Aug. 30, 1993 and entitled "Malleable Fracture Stabilization Device with Micropores for Directed Drug Delivery" has disclosed a two layered device that contains a first layer of minimally porous material affixed to a second layer of medication-containing material. This two-layered device is capable of performing several functions simultaneously.

The Malleable Fracture Stabilization Device with Micropores for Directed Drug Delivery is a malleable fixation device that, when wrapped around or affixed to fractured tissues, holds the fragments in tight register while delivering any of a number of medications directly and specifically to the interfragmentary space. It is designed to be used with existing orthopedic devices that provide rigid fixation of major fracture fragments. With the Malleable Fracture Stabilization Device with Micropores, heterotopic bone formation is minimized, since both the exogenous (supplied by the invention) and endogenous (supplied by the native healing tissue) growth factors are directed preferentially into the fracture site. The Malleable Fracture Stabilization Device with Micropores is provided as a flexible two layered sheet that the surgeon in the operating room can staple, suture or otherwise affix to the injured site as each particular case demands.

The Malleable Fracture Stabilization Device with Micropores can deliver medicines, including growth factors, chemotheraputic agents and antibiotics, directly into the site of injury. It can also permit the free passage of small molecules such as water, small ions, glucose and urea through the device. The Malleable Fracture Stabilization Device with Micropores can approximate and stabilize tissue fragments and can be molded by the surgeon in the operating room to fit the site of injury. The flexible and semi-soft nature of this device also provides means to administer additional medicine to the site of injury at a later time. In addition, the "Malleable Fracture Stabilization Device with Micropores for Directed Drug Delivery" can be used to: 1) Deliver local chemotherapy into curettage sites or to soft tissue metastases. 2) Deliver local antibiotics to sites of infection. 3) Increase the speed of bridging between prosthetic or allograft and native tissue.

Improvements to the Malleable Fracture Stabilization Device with Micropores for Directed Drug Delivery Although the "Malleable Fracture Stabilization Device with Micropores for Directed Drug Delivery", solves many problems not addressed by the prior art, several improvements in design can be made to make it even more desirable as a healing agent. Specifically, it would be desirable to make the device a single layer so that less foreign material be implanted into the patient. It would also be desirable to have the treating material released in a more controlled manner than mechanical efflux from pores. It would be also be advantageous to make the device as thin as possible such that it can be more easily delivered percutaneously through an endoscope, a hollow needle or a catheter. Finally, it would be desirable to be able to apply the device as a spray such that contact between the device and the tissue is maximized.

The present invention is provided as a single-layered, malleable fixation device that, when wrapped around or affixed to fractured tissues, holds the fragments in tight register while containing macromolecules produced by the injured tissue at the site of injury where they are needed most. This device, like the Malleable Fracture Stabilization Device with Micropores for Directed Drug Delivery, permits the free passage of small metabolites and water through pores in the device. When a treating material is affixed to the provided device, the device can deliver it directly and specifically to the fracture site. Medicines, when they are diffusable macromolecules, can be held to the single layer using chemical bonds such that medicines are released according to a rate constant rather than random diffusion through a matrix of pores. The device is soft enough that a needle can pierce it to administer additional medicine or to sample the fluid in the interfragmentary space without the need for reoperation.

This invention is designed to be used with existing orthopedic devices when rigid fixation of major fracture fragments is required. With this invention heterotopic bone formation is minimized, since both the endogenous and exogenous growth factors continue to be directed preferentially into the interfragmentary space. This invention is to be provided as a flexible sheet, spray or tube that the surgeon in the operating room can staple, suture or otherwise affix to the injured site as each particular case demands.

The reader will further appreciate several additional uses of the invention that can be performed with only slight modification of the basic structure of the present device. These uses include, but are not limited to the treatment of metastases, infections, metabolic disorders of bone such as osteoporosis, primary neoplasms and vascular disease. This invention can be used in conjunction with other fixation devices and implantables to augment their function and improve their healing efficacy. It is these improvements that I wish to discuss in the present application.

Objectives of the present invention:

It is a principal object of the present invention to provide a unique method of tissue stabilization and containment of interfragmentary macromolecules using a single, flexible minimally porous sheet.

It is a further object of the present invention to provide a unique method and apparatus that can perform the essential healing features of the Malleable Fracture Stabilization Device with Micropores for Directed Drug Delivery using only a single layer of minimally-porous layer to which has been affixed a treating material directly on its surface.

It is a further object of the present invention to provide a unique method and apparatus for internal treatment of fractured tissues that can be delivered via a percutaneous delivery system.

It is a further object of the present invention to provide a unique method and apparatus for internal treatment of fractured tissues that can be applied as a spray film.

It is a further object of the present invention to provide a unique method and apparatus that can be affixed to an intramedullary rod such that a treating material can be delivered from within the medullary cavity and bony bridging between the fracture and the prosthetic can be minimized allowing for easier removal of a rod, plate or screw.

It is a further object of the present invention to provide a unique method and apparatus that can be deployed via endoscope, catheter, or open surgical procedure that can serve both to preferentially direct endogenous macromolecules and release treating materials while also providing structural support to hollow viscera, solid organs, or blood vessels.

Other objects and advantages of the invention will be apparent from the following summary and detailed description of the fracture stabilization device and of the methodology applicable to its use taken together with the accompanying drawing Figures.

SUMMARY OF THE INVENTION

The invention is a unique method of fracture stabilization and way to restrain interfragmentary macromolecules using a single, flexible minimally porous sheet.

I have found that a cardinal feature of the Malleable Fracture Stabilization Device with Micropores for Directed Drug Delivery is its ability to restrain macromolecules produced by the fracture within the interfragmentary space. Although the macromolecular restrainment means of the Malleable Fracture Stabilization Device with Micropores is a feature of its minimally-porous layer, the present invention is remarkable in that it accomplishes this task using a single sheet, rather than a two layered sheet.

Because a fundamental tenant of surgical practice to keep the amount of foreign material placed within the body to an absolute minimum, any decrease in the amount of implant used is of benefit to the patient. Therefore, the elimination of an entire layer while maintaining function is a highly significant improvement in design. By eliminating a large percentage of the mass of prosthetic necessary to perform the same function, the device used in the present invention becomes even more hospitable to both the patient and the surgeon.

According to one embodiment, a single sheet that is flexible in three dimensions and minimally porous to macromolecules, is wrapped around or affixed to a fractured tissue. The device subsequently maintains a substantially higher concentration of macromolecules produced by the fracture within the interfragmentary space or chamber compared to that within the surrounding soft tissues. For example, if one were to measure the concentration of a selected growth factor produced by the fractured tissue across the single layer of the device, the concentration of that factor would be substantially greater on the side adjacent to the fracture compared with the side adjacent to the neighboring soft tissues.

Although the precise size of the molecules that the minimally-porous sheet can restrain is not important, for the purposes of this invention the pores should be small enough to restrain molecules greater than around 500 Daltons. In fact, the device can be manufactured in such a way to vary the pore size depending on the molecules one would like to restrain. For example, if a surgeon wishes to restrain molecules weighing 10,000 Daltons, he or she would ask for the device with a 5,000 MW pore size to be taken off the shelf and opened for use. The device can be manufactured with a multitude of different pore sizes or have different pore sizes within different regions of single sheet.

Another surprising feature of this invention is that it can be manufactured to selectively restrain molecules of a particular ionic charge regardless of pore size. In this embodiment, during manufacturing the device can be made of molecules with, for example, positively-charged groups on its surface. If the surgeon wished to restrain molecules with a particular charge, he or she would ask for a device manufactured in this manner. If the device is made of a hydrophobic material, fatty macromolecules such as steroids can be restrained.

The invention is a unique method and apparatus that can perform the essential healing features of the Malleable Fracture Stabilization Device using only a single layer of minimally-porous material to which has been affixed a treating material directly on its surface.

According to another embodiment of this invention, a treating material is affixed directly to one surface of the minimally-porous sheet. My Malleable Fracture Stabilization Device requires that a second microporous layer containing a treating material be affixed to the minimally-porous layer. I have found unexpectedly that, if one affixes medicine directly to the minimally-porous layer, one can bypass the need for the microporous layer entirely! For example, if one chemically binds the medicine to the minimally-porous layer using a particular type of chemical bond, the bonds will be hydrolyzed in situ according to a specific rate constant. If one wishes to release medicine into the interfragmentary space at different rates, one simply has to manufacture the device with bonds that become hydrolyzed at a different rate. Like the Malleable Fracture Stabilization Device with Micropores, one can also deliver treating energy, e.g., radiofrequency, in a directional manner simply by coating the invention with an energy sink on the side away from the tissues that you wish to treat.

This single layered design has, by itself, several advantages over the two layered Malleable Fracture Stabilization Device with Micropores. First, because the need for a separate microporous layer has been eliminated, the patient has less foreign material implanted in his/her body. Second, the material delivery rate is much more uniform when a chemical reaction determines the release rate rather than passage through a mechanical pore. Third, because the need for an entire layer has been eliminated, the device can be manufactured much thinner than the two-layered Malleable Fracture Stabilization Device with Micropores.

The invention can be made much thinner than state-of-the-art fixation devices

One problem with placing any device into the body is the need to displace normal structures to make room for the device. Although percutaneous deployment can be accomplished with my Malleable Fracture Stabilization Device with Micropores, it follows that the smaller and thinner the device, the less damage is going to occur when it is being installed. If the device is too large, it physically cannot be made to fit into small spaces. For example, an intramedullary rod cannot be used to fix skull fractures because the skull does not have a large enough medullary space. If one wishes to squeeze a device into small crevices between tissues or through small introducer needles when placing into the body, it is clear that a smaller and thinner device is better than a large and thick one. For this reason, this invention is preferable to my Malleable Fracture Stabilization Device with Micropores for use in small spaces such as within small hollow viscera or blood vessels.

The invention is thin enough to be introduced into the medullary cavity, blood vessels and hollow viscera using a percutaneous delivery system.

I have discovered that, if one manufactures the invention as a very thin sheet, one can roll it up and put it into a catheter or introducer needle such that it can be deployed percutaneously. When the device is deployed, it unrolls and becomes deposited intimately against the inner wall of the bone, the vessel wall or the hollow viscera lumen. Healing macromolecules can be contained at the site of injury, and medicine can be applied directly and preferentially to an injured wall to promote healing. If this invention is manufactured as a stent, structural support and macromolecular containment, and even directional and preferential drug delivery can also be provided (current state-of-the-art stents are either porous meshes, e.g., Wallstent™ and Gianturco-Rosch COOK-Z™, or do not have "macromolecular containment means and/or "directional delivery means", e.g., Scott et al., U.S. Pat. No. 5,383,928).

The unexpected ability of this invention to fit into an introducer needle also allows one to treat inflammatory conditions and metabolic conditions percutaneously. For example, this invention coated with antibiotics can be placed within an abscess cavity and placed directly adjacent to the abscess wall. One can then administer antibiotics in a directional manner in timed-release fashion at the site they are needed most. One can also treat metabolic conditions such as osteoporosis locally by introducing this invention either within the medullary cavity or adjacent to the periosteum in areas high risk for fracture. One would simply need to direct the medication coated side appropriately. This technique can provide rapid, directed therapy to areas of high risk for fracture without need for operation.

This invention can also be deployed via endoscope or introducer needle to treat solid organs, e.g., liver and biliary system, or hollow organs such as the esophagus.

BRIEF DESCRIPTION OF THE DRAWINGS

FIG. 2b This shows an embodiment of the invention by which the restrainment means have been accomplished using electric charge. Note that some molecules can pass through the invention virtually unhindered, while others are restrained within the interfragmentary space.

FIG. 8f This is a cross section view of the embodiment shown in FIG. 8e. Note that although water and small metabolites are free to move across the device, the concentration of both medicine and endogenous macromolecules in the space between the device and the inner wall is markedly greater than the concentration of these molecules within the lumen. The dashed box, "A", is magnified in FIG. 8g.

FIG. 8h This drawing shows a high-power view of the boxed area "A" of FIG. 8d. Note that not only are the endogenous macromolecules and treating materials kept in this space instead of diffusing into the lumen, but water and small metabolites are free to move across the device as shown in FIG. 3a.

REFERENCE NUMERALS

Figure 1A:
FIG. 1a This is a side view of the device of the present invention provided as a sterile, single-layered, flexible, minimally-porous sheet having macromolecular restrainment means. Note that it is a single layer of minimally-porous material, rather than a two layered structure.

1) Single-layered, flexible, minimally-porous sheet having macromolecular restrainment means
2) Flexible, microporous, treating material-containing component of the Malleable Fracture Stabilization Device with Micropores for Directed Drug Delivery (prior art, U.S. application Ser. No. 08/114,745, Filing date Aug. 30, 1993).
3) Flexible, minimally-porous sheet with macromolecular restrainment means component of Malleable Fracture Stabilization Device with Micropores for Directed Drug Delivery
4) Interfragmentary space or chamber
5) Minor fracture fragment
6) Staple
7) Major fracture fragment
8) Macromolecules produced by injured tissue
9) Solid intramedullary rod
10) Treating material in solution
11) Infected, cancerous or otherwise abnormal tissue
12) Treating material affixed to single-layered, flexible, minimally-porous sheet
13) Healthy, uninjured tissue
14) Region outside of the interfragmentary space which is on the opposite side of the invention.
15) Energy sink, i.e., directional delivery means for radiofrequency or radioactivity
16) Small metabolites
17) Passage means or pores for small metabolites
18) Atherosclerotic plaque
19) Molecules unaffected by the charge of the invention.
20) Molecules restrained by the positively-charged sheet
21) Positively-charged, single-layered, flexible, minimally-porous sheet.
23) Energy unit, e.g., Radiofrequency energy
24) Chemical bond
25) Abscess cavity
26) Fenestrated intramedullary rod
27) Space or hole between the mesh of the Gianturco-Rosch COOK-Z™ stent (prior art)
28) Support ring of the Gianturco-Rosch COOK-Z™ stent (prior art)
29) Support strut of the Gianturco-Rosch COOK-Z™ stent (prior art).
31) Spray stream that forms the invention when the spray hits a solid surface.
32) Spray can containing liquid or vaporized components of the invention.

33) Lesser sac
34) Greater sac
35) Spleen
36) Kidney
37) Inflatable balloon
38) Inner lumen of hollow organ
39) Wall of blood vessel
40) Space or hol between invention and the injured tissue
41) Pancreatic head tumor
42) Duodenum
43) Pancreas
44) Gall bladder
45) Common bile duct
46) Liver
47) Skin
48) Introducer needle
49) Kelley clamp
50) Energy introducer conduit

DESCRIPTION OF THE PREFERRED EMBODIMENTS

This invention is designed to keep small tissue fragments, cells, and the macromolecules they produce in the space between fracture fragments, i.e., the interfragmentary space, and out of neighboring soft tissues. When the method of use contains the additional step of affixing a medicine to the flexible macromolecular-containment device prior to implantation, additional healing benefit can be realized because, not only are the macromolecules produced by the fracture contained within the interfragmentary space, but additional medicines beneficial to the healing process can be delivered directly and preferentially into the fracture site. Moreover, because the device can be made of a soft fabric, a needle can be passed through the device and additional treating materials can be repeatedly injected into and contained within the interfragmentary space long after the device has been implanted.

Structure of the device used in the invention:

The device, 1, is composed of a single sheet of material that in its principal embodiment is supplied as a thin, pliable, fabric that is flexible in three dimensions by human hands. The device itself must be substantially impermeable to macromolecules, 8, such that they are preferentially concentrated within the interfragmentary space, 4. The precise size of the macromolecules that are preferentially restrained is not important, but they should probably be greater than 500 molecular weight. The idea is that small metabolites, 16, such as water, urea, bicarbonate, and hydrogen ions are free to pass through the device to leave the interfragmentary space, 4.

The method by which this preferential restrainment of macromolecules is accomplished is by varying the size and number of the pores, 17, in the minimally-porous sheet. The device should also be a strong enough fabric that it is capable of holding small or minor fracture fragments, 5, substantially in the plane formed by the major structure fragments, 7.

Figure 1B:
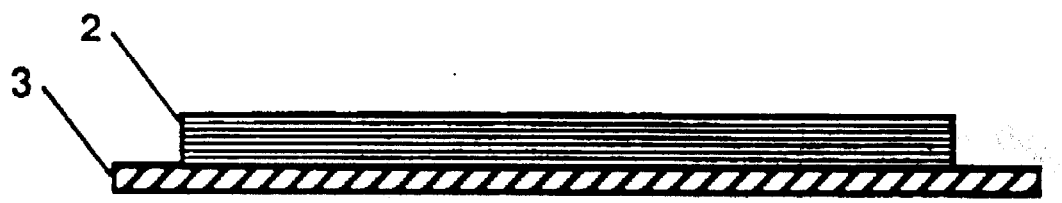
FIG. 1b This is a side view of the two-layered Malleable Fracture Stabilization Device with Micropores for Directed Drug Delivery (prior art, U.S. application Ser. No. 08/114, 745, Filing date Aug. 30, 1993). Note that it is thicker and contains more structural materials than the present invention.
Figure 1C:
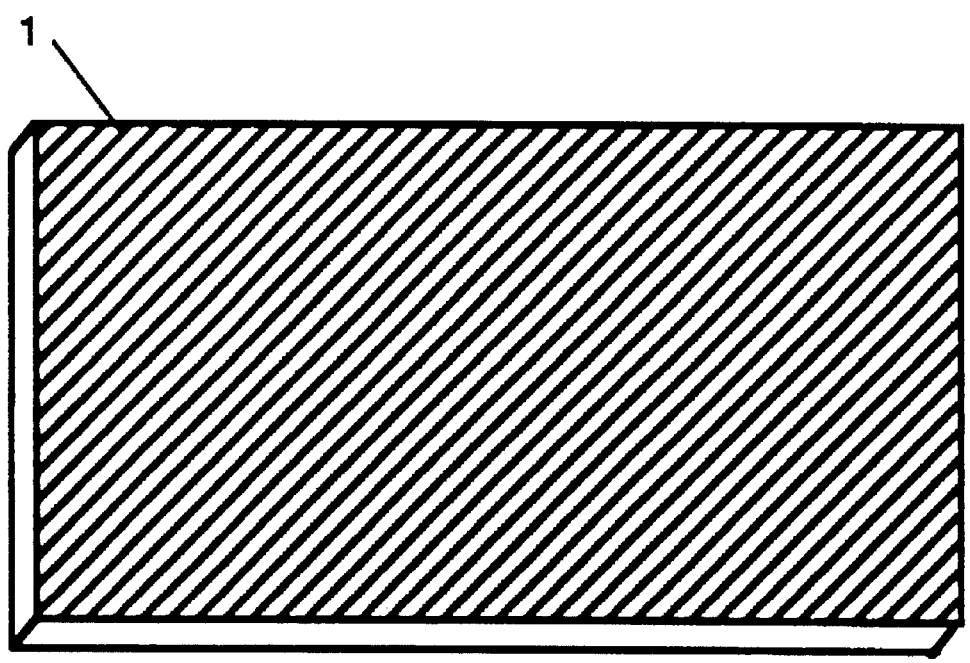
FIG. 1c This is a top view of the present invention, which is provided as a single-layered, flexible, minimally-porous sheet having macromolecular restrainment means. It is obliqued slightly to show that the invention has depth.

FIG. 1a shows the device, 1, in profile prior to implantation into a patient. Note that it is a single, thin layer of material as opposed to the structure of the Malleable Fracture Stabilization Device with Micropores for Directed Drug Delivery (U.S. patent application Ser. No. 08/114745, filed Aug. 30, 1993) shown in FIG. 1b. Surprisingly, I have been able to eliminate the need for the Microporous layer, 2, without sacrificing the utility and capability of the parent device. The principal embodiment of the present invention is a sheet with the same characteristics as the malleable, minimally-porous anchoring component, 3, of the Malleable Fracture Stabilization Device with Micropores. As the reader will appreciate, the device of the present invention is much thinner than the Malleable Fracture Stabilization Device with Micropores, a fact that will yield surprising advantages when it comes time to deploy it in a patient. FIG. 1c shows a top view of the device.

Figure 2A:
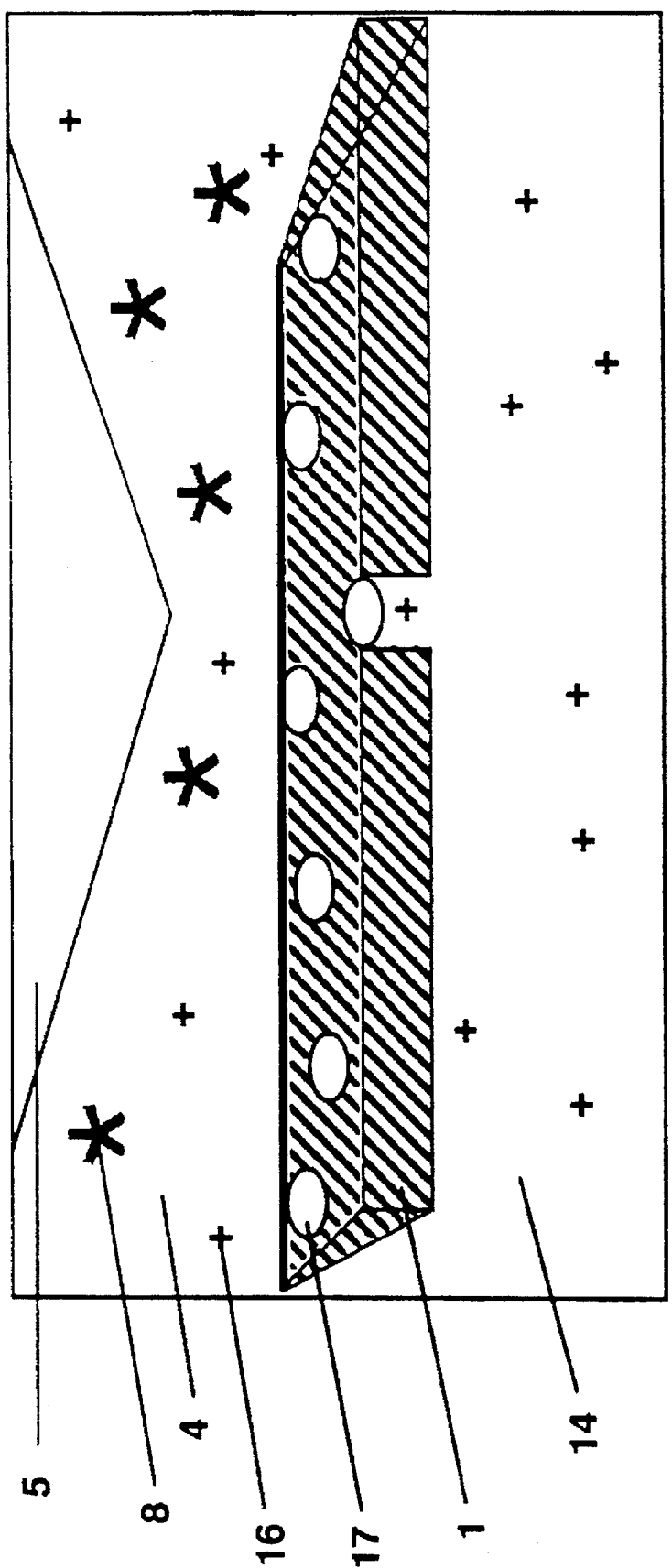
FIG. 2a This shows a key element of the invention, the selective passage of some molecules with the restrainment of others. The "restrainment means" of the present invention are such that some molecules can pass through unhindered, while others are markedly contained within the interfragmentary space.

FIG. 2 displays a critical aspect of the present invention, the means for minimal-porosity and macromolecular containment, 17, i.e., the pores. In FIG. 2a, note that within the interfragmentary space, 4, there is a substantially-higher concentration of the macromolecules produced by the fractured tissue, 8, than in the region outside of the interfragmentary space, 14. Also note that small metabolites, 16, are free to move through the pores of the device, distributing themselves in approximately equal concentration across the device. Once these metabolites pass through the device, they are rapidly carried away via the blood. Remarkably, the minimally-porous nature of this device serves the same function of kidney dialysis, except in the local fracture environment. The "dialysis" of metabolites away from the interfragmentary space actually forces the equilibrium towards production of more metabolites, thereby speeding healing. Although this "dialysis" function occurs with the Malleable Fracture Stabilization Device with Micropores, I have found surprisingly that this process occurs more rapidly and more efficiently without the microporous layer in the way. FIG. 2b depicts the same concept, except that the device has either been coated with or been made of a substance having an electric charge, 21. Molecules are subsequently restrained, 20, or are allowed to pass through, 19, the device based on their electric charge rather than by their size.

Attachment of a treating material to the device of the invention:

I have found unexpectedly that medicine or other treating materials can be attached directly to the flexible, minimally-porous sheet of the Malleable Fracture Stabilization Device with Micropores. The ability of medications to stick to the single sheet of minimally-porous material was surprising, and has provided an exciting series of improvements in both medicine release and in the ease of deployment.

Figure 3A:
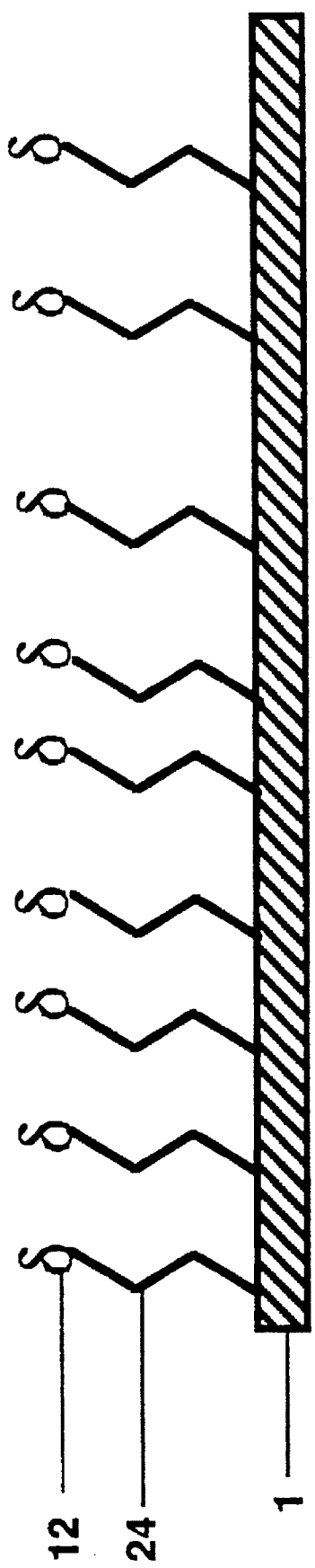
FIG. 3a This drawing shows an embodiment in which a treating material has been affixed to the invention. In this example, medicine is attached to the invention using a hydrolyzable chemical bond.
Figure 3B:
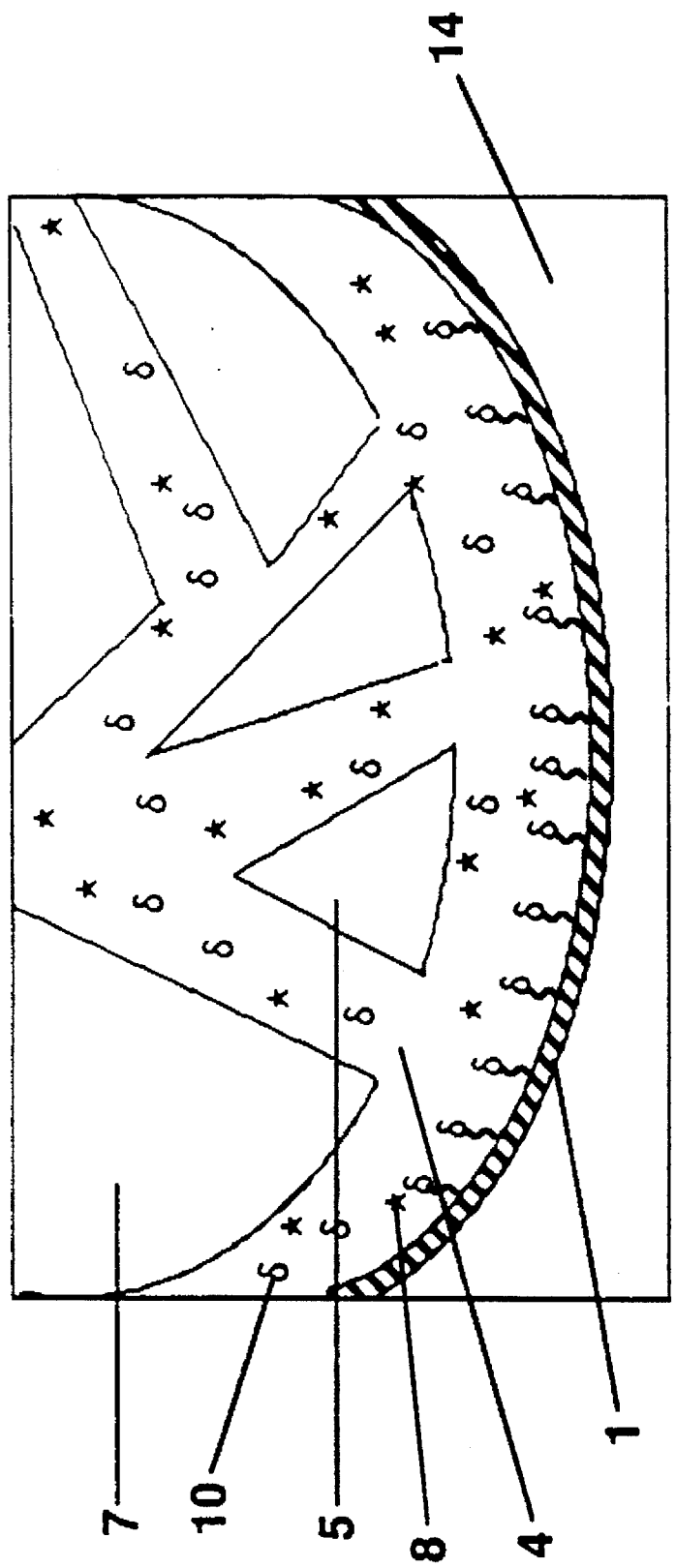
FIG. 3b This drawing shows a medication-containing embodiment of the invention treating an injured bone. The medication containing side is adjacent to the injury site. Because the device is impermeable to both the treating material and the macromolecules produced by the fracture, the concentration of both types of macromolecules is substantially higher in the interfragmentary space compared to that within the surrounding soft tissues.

FIG. 3a shows a magnified view of FIG. 1a with the additional feature of a medicine, 12, that has been affixed to the invention by means of a chemical bond, 24. FIG. 3b depicts the device with this embodiment in use. Note that both the macromolecules produced by the fracture, 8, and the treating, or material in solution 10, are restrained within the interfragmentary space, 4. As with the Malleable Fracture Stabilization Device with Micropores (but in distinction to the device of Scott et al., U.S. Pat. No. 5,383,928), this device has the capability of directional release.

A surprising new feature of this device is the improvement in the medicine release kinetics compared to the prior art. Whereas both the stent sheath of Scott et al. (FIG. 8d) and the microporous layer of the Malleable Fracture Stabilization Device with Micropores, 2, rely on the random diffusion of medicine from micropores, I have found that I can achieve a prolonged duration and much more stable rate of efflux from the device when medicine is attached using a hydrolyzable bond. In fact, by using a chemical reaction to provide medicine release means, medicine is released into solution proportional to the rate constant of the reaction. Release rates can be adjusted simply by varying the linkage between the medicine and the device. In the preferred embodiment, these linkages are hydrolyzable by the water within the interfragmentary space; however the linkages can be made of any suitable bond, e.g., a bond that requires a particular enzyme for hydrolysis. Surprisingly, by using bonds that require an enzyme provided only by osteoblasts, one can delay the release of the medicine from the device until the osteoblasts arrive.

This device can be manufactured with several different medicines, each with their own particular release bond. Remarkably, one can implant the device of this invention such that one medicine is released by enzymes from Neutrophils (the first inflammatory cells to arrive), a second medicine released by enzymes from fibroblasts (cells that arrive later), and a third medicine which can be released only by osteoblasts (cells arriving even later). Although I have disclosed the implantation of multiple medicines in my application for the Malleable Fracture Stabilization Device with Micropores, the surprising specificity of medicine release provided by the chemical bond is entirely new and unexpected The above-described feature of specific drug release is impossible using the prior art, and it represents a major advance in fracture treatment.

Materials suitable for device manufacture:

Several types of materials can be used in the manufacture of the device. One suitable material is a modification of nylon; however it can be manufactured with any other material that meets the criteria of minimal-porosity and macromolecular containment including but not limited to metal, a metal alloy, a plastic, a synthetic polymer, a biological polymer, or a biodegradable biological polymer, an element, e.g., a matrix formed of carbon, a polymer, a ceramic, a surgical gut, a gelatin, a collagen, living tissue, synthetic tissue, non-living tissue, and a polymer resorbable by living tissue.

Suitable resorbable polymers include but are not limited to polyglycolides (PGA), polylactones, polycarbonates, polyesters of oxalic acid, polylactides (PLA), poly β hydroxybuteric acids (PHBA), polyesteramides (PEA), glycolic esters, polyethers, cyanacrylates, poly β hydroxypropionic acids (PHPA), poly β hydroxyvaleric acids (PHVA), poly p dioxanones (PDS), or chitine polymers.

The thickness of the material is typically 0.1 mm to 2.5 mm although the thickness is not important as long as the device has the features of minimal porosity and macromolecular containment as described. The dimensions of the device are variable and depend on each particular clinical application; however for a comminuted femoral fracture the dimensions would be approximately 20 cm×10 cm. The device can be biodegradable or inert. The invention can, depending on the materials of which it is composed, either be removed surgically at a later time, or resorb in situ, over the course of weeks to months.

The only requirements are that the material be
1) Biologically compatible and not prohibitively toxic during its tenure in the body.
2) Flexible in three dimensions by human hands and can be bent, shaped, and/or cut in the operating room.
3) Minimally porous as described above such that it is capable of substantially containing macromolecules on one side of the device.
4) Substantially porous to small molecules such as metabolites Treating materials suitable for use with this device:

Any number of medicines can be used in the application of this device. Although originally engineered to deliver bone growth factors, the device can deliver any of a number of treating materials including but not limited to bone morphogenetic proteins, nerve growth factors, extracellular matrix components, e.g., fibronectin and laminin, connective tissue growth factors such as fibroblast growth factors, antibiotics, vitamins, cofactors, a growth factor, a glycosaminoglycan, a bioactive ion, nuclear or ionic radiation, radiofrequency, a molecule produced by fractured tissue, a pharmaceutical, a hormone, and living cells—either wild-type or genetically engineered.

Figure 4A:
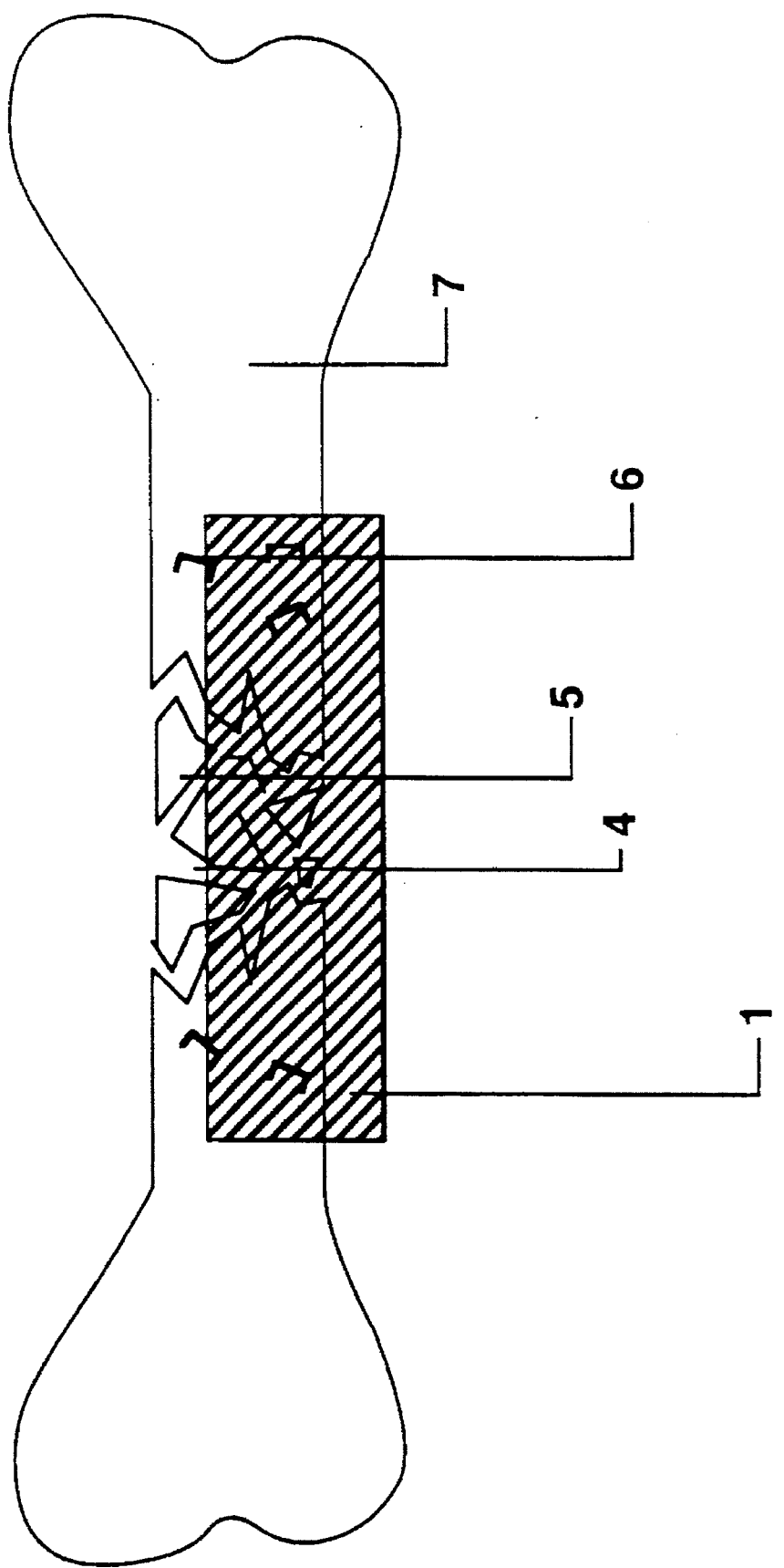
FIG. 4a This is a side view of the single-layered, flexible, minimally-porous sheet with macromolecular restrainment means wrapped partially around a comminuted bone fracture. In this embodiment, the invention has been affixed to the bone with staples.

Operation of the Invention:

FIG. 4 shows show the device wrapped around a comminuted fracture of a long bone. The invention is to be provided as a sterile sheet (FIGS. 1a and 1c, or FIG. 2b or FIG. 3a) A typical example of the circumstances of use of this invention is as follows:

A patient arrives in the emergency department after being hit by a car. X-rays of his right leg reveal a severely shattered right femur. An orthopedic surgeon takes the patient to the operating room to fix the fracture. He/she then exposes the fracture and elects to stabilize the major components of the fracture, 7, using an intramedullary rod. He/she then selects the Single, Flexible, Minimally Porous Sheet of this invention to which has been affixed a combination of penicillin, bone morphogenetic protein, Fibroblast Growth Factor, and Transforming Growth Factor Beta, to stabilize and prevent resorption of the minor fragments, 5. He/she then wraps the sheet around the fracture with the medicine side directed in. The surgeon then tightens and secures the device with staples, 6, such that the fragments are held tightly together and in anatomic alignment. The size of sheet to be selected should be sufficient to overlap the ends of the major fragments both proximal and distal to the fracture fragments as is shown in FIG. 4a.

The invention is to be provided in several different sizes, and with several different pore sizes and with several different combinations of medicines affixed. In the operating room, the surgeon need only choose the appropriate size sheet and the preferred macromolecules he/she wishes to restrain and deliver. The invention can be twisted, bent or cut to meet the exact requirements of the injury. The strength of the sheet provides the necessary strength to hold the small fragments in line. The surgeon affixes the device to the injured tissues using staples, sutures or bands according to his/her preference. The object is to wrap the device around the fracture as completely and as tightly as possible such that there is sufficient pressure on the fracture hematoma that small fragments are substantially contained within the major plane of the fracture. This device can, depending on the materials of which it is composed, either be left in place permanently, be removed surgically at a later time, or resorb in situ, over the course of weeks to months.

Figure 4B:
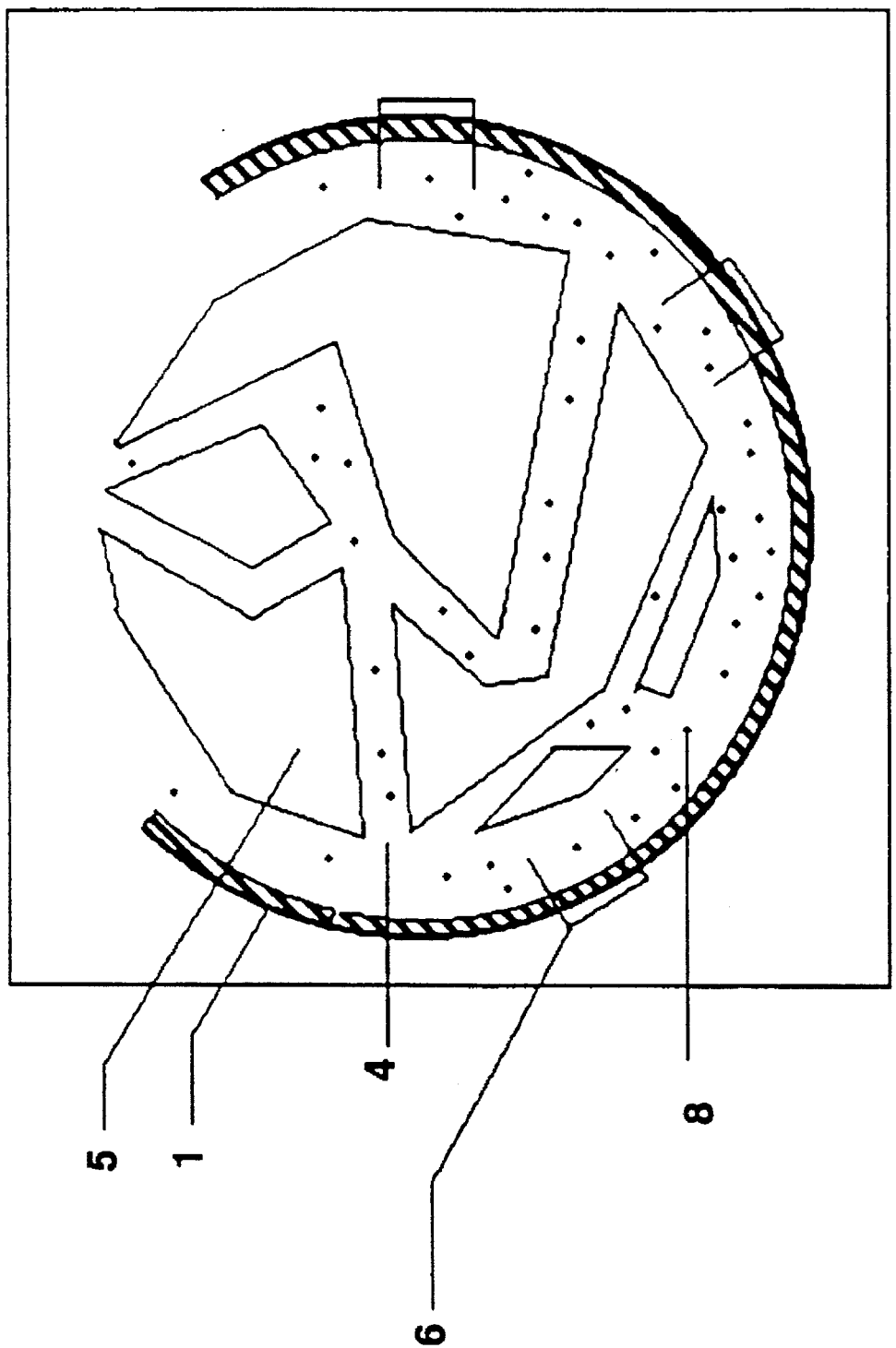
FIG. 4b This is a cross sectional view of the invention taken through the area of shattered bone. The macromolecules produced by the fracture have been substantially contained within the interfragmentary space. Note also that the minor fragments of the fracture have been held in line with the major fragments to facilitate bony bridging.
Figure 4C:
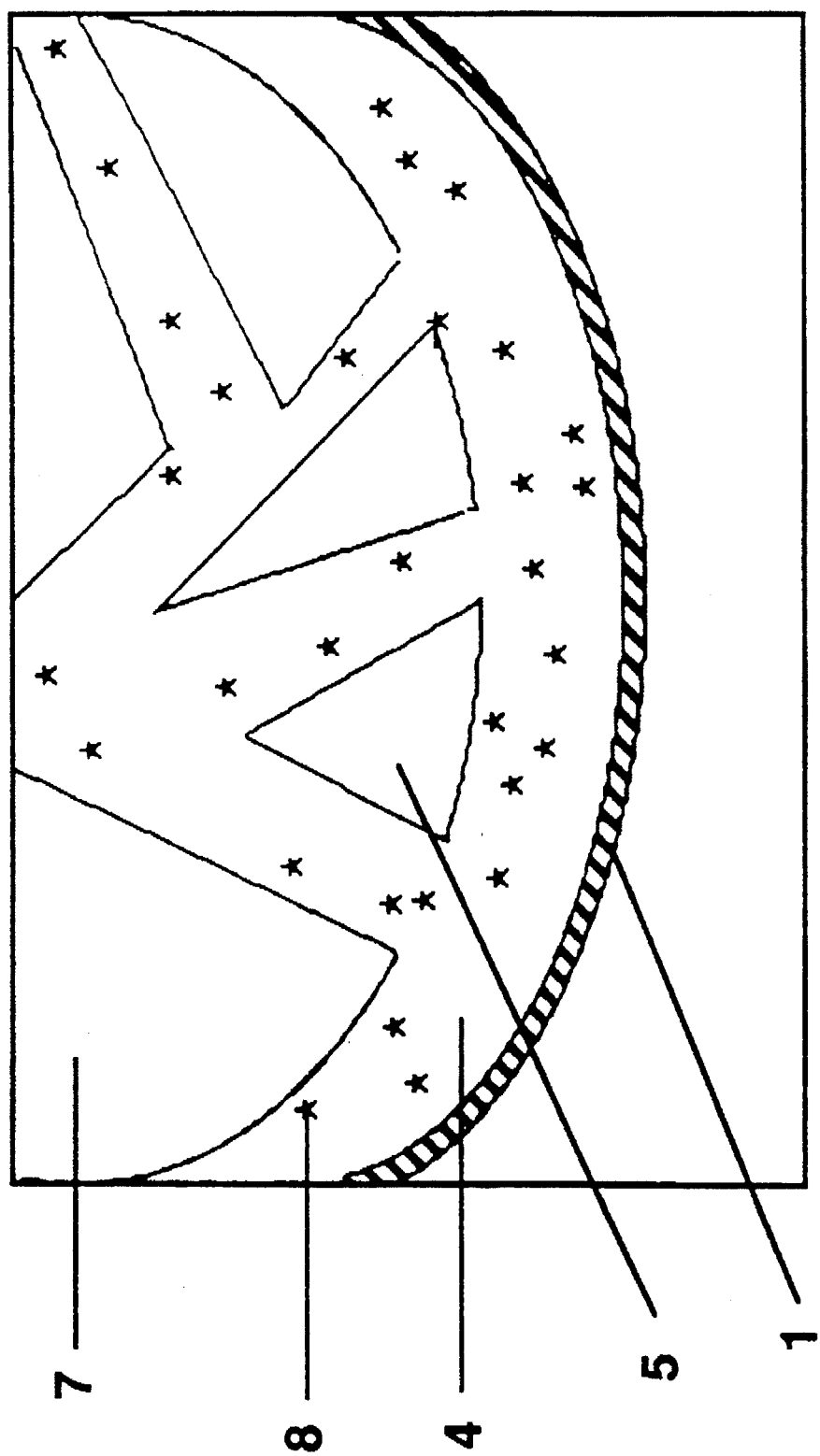
FIG. 4c This is a close-up view of the interface between the invention and the injured bone. Again notice that the macromolecules produced by the fracture are substantially contained within the interfragmentary space and that small fragments are held in close proximity to the major fragments.

FIG. 4b shows a cross section of the fracture illustrated in FIG. 3a taken through a point of comminution. Notice that the macromolecules produced by the fracture, 8, are substantially contained within the interfragmentary space, 4. In the provided example, the device is not completely wrapped around the bone. If muscles attached to the femur are present, they need not be dissected away for the device to work. FIG. 4c is a close up view of the device-bone interface. Note that the minor fracture fragments, 5, as well as the interfragmentary macromolecules, 8, are maintained in close proximity to the major fracture fragment, 7.

This device, like the Malleable Fracture Stabilization Device with Micropores, can also be used to increase the speed of fusion between bone grafts and native bone, between prosthetic devices, e.g., total hip replacement prostheses and native bone, and between allograft and native bone.

Intramedullary deployment of the invention:

A surprising and particularly useful sequela of eliminating the microporous layer of the Malleable Fracture Stabilization Device with Micropores, is the ability to make the device considerably thinner. This ability provides several new and unexpected applications which I will discuss below.

Figure 5A:
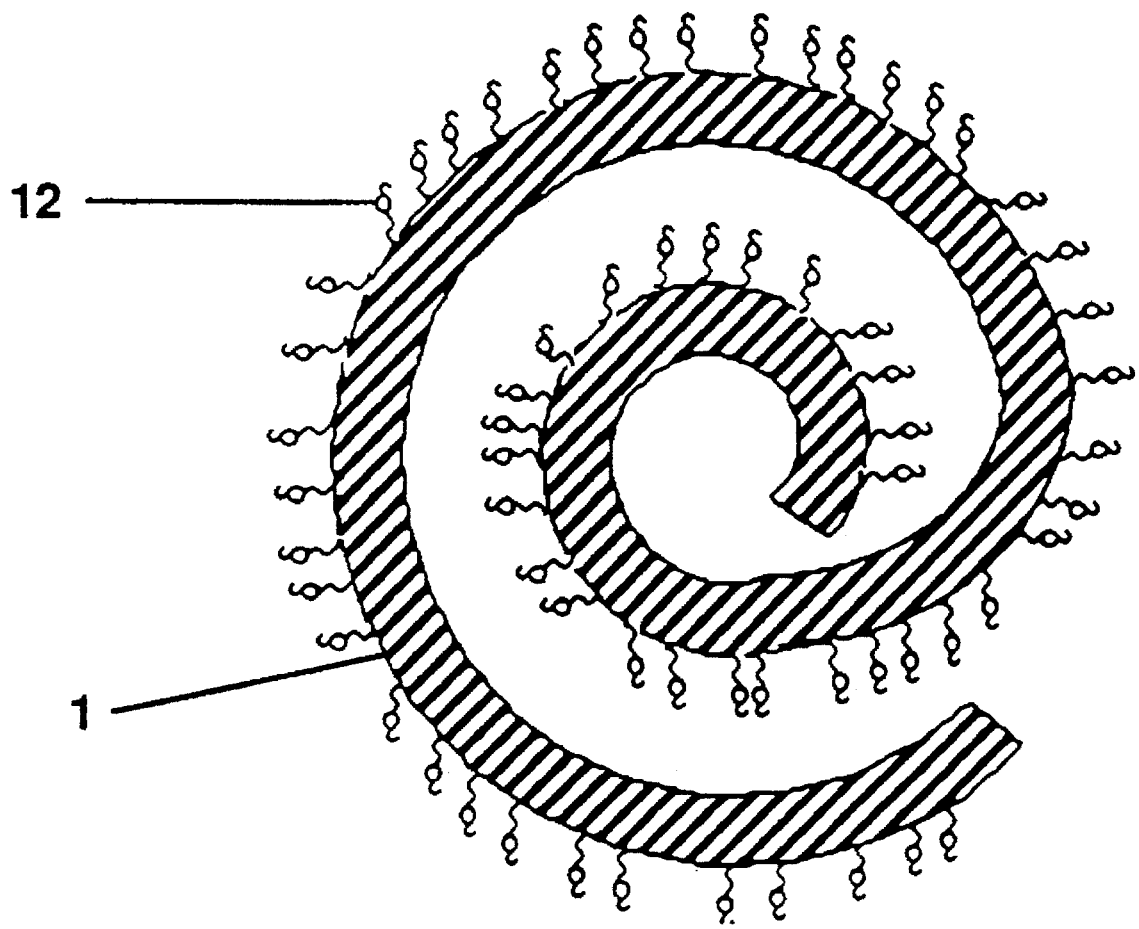
FIG. 5a This shows a medication-containing embodiment of the invention that has been rolled up. The number of turns is not important.
Figure 5B:
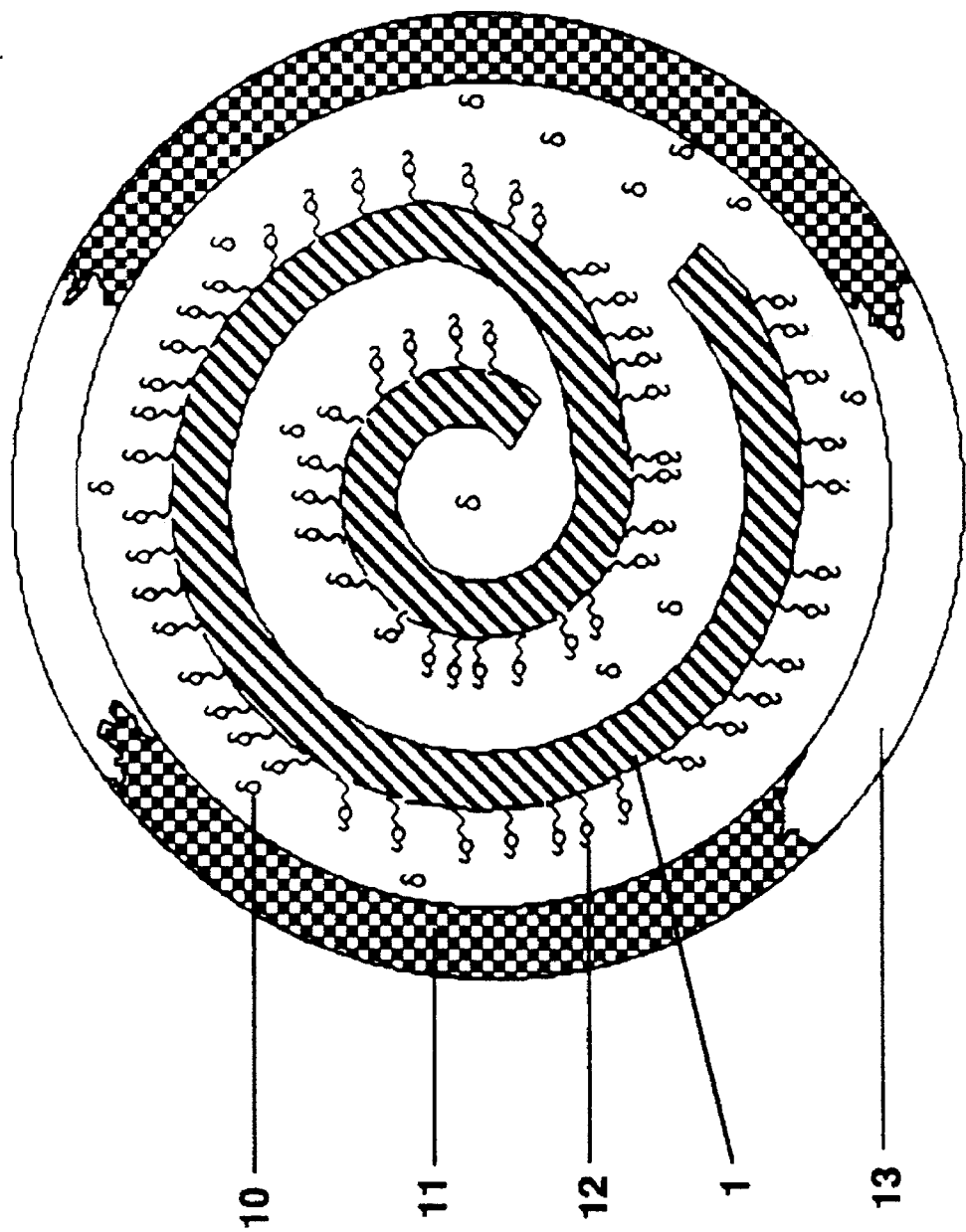
FIG. 5b In this example, the invention has been placed within the medullary cavity of a long bone with the medicine directed out. Note that the medicine is intimately associated with the abnormal tissue. The macromolecular containment means serves to keep the medicine where it is most needed. Furthermore, abnormal cells or the products they produce can be restrained by the macromolecular containment means of the device. As with the Malleable Fracture Stabilization Device with Micropores, water and small metabolites are free to move across the device.

One difficulty in the treatment of complex fractures lies in exposing the fracture. I have found unexpectedly that treating materials can be delivered to a fracture "inside out" if one places this invention either within a hollowed out and fenestrated IM rod, or pushes the invention into the medullary cavity. FIG. 5a illustrates the invention rolled up after it has been coated with medicine. Note that when the device unrolls, the medicine affixed to the surface will be directed out. A balloon catheter can be passed through the vertex of the roll to maximally appose the device to the injured tissue. FIG. 5b can be used to illustrate two examples of intramedullary treatment.

The invention can be used to treat metastases:

FIG. 5b can depict the treatment of cancer that has metastasized to bone. In this application, "12" represents an anti metabolite directed to the abnormal tissue or bone, 11. Because the therapeutic window of systemic chemotherapy is very narrow (even if it is administered in the correct dosage, side effects can be both dangerous and unpleasant), the holy grail of cancer treatment is to get the highest allowable concentration of chemotherapy to the places it will do the most good. This invention can be used to deliver chemotherapeutic medicines directly and specifically to metastatic deposits, and can deliver them in a timed-release fashion. The reader will appreciate that, since these molecules can be restrained against the tumor and largely kept out of the systemic circulation, a much greater concentration can be administered using this device. In the same vein, radionuclides can also be administered in this fashion.

This invention can also be wrapped around the abnormal bone much like in the treatment of a fracture. I have found unexpectedly that if the device is made of a non-resorbable material such as silicone rubber or ethylene vinyl acetate, one can repeatedly pass a needle through the device and inject more medicine into the space between the device and the bone. Because the device is only minimally-porous to the chemotherapy macromolecules, a patient can use this invention as a reservoir to locally treat a troublesome bone met, getting periodic refills at his/her oncologists office. In this way, not only would the patient avoid additional systemic chemotherapy, but he/she might also avoid a pathologic fracture and the morbidity associated with an open surgical procedure to fix it.

The invention can be used to treat osteomyelitis:

FIG. 5b can also be used to depict the invention rolled up inside the medullary cavity of a long bone that is infected. The device has unrolled and now is apposed to the inner surface of the abnormal tissue or bone, 11. In this embodiment, antibiotic can be delivered preferentially to the infected bone in much higher concentrations than would be possible using systemic therapy. Healthy tissue or bone is also shown 13. Because metabolic activity in an area of infection is so high, it is critically important that metabolites be able to cross the device and be removed from the scene rapidly. As the reader can appreciate, the invention is perfectly suited for this purpose.

Figure 5C:
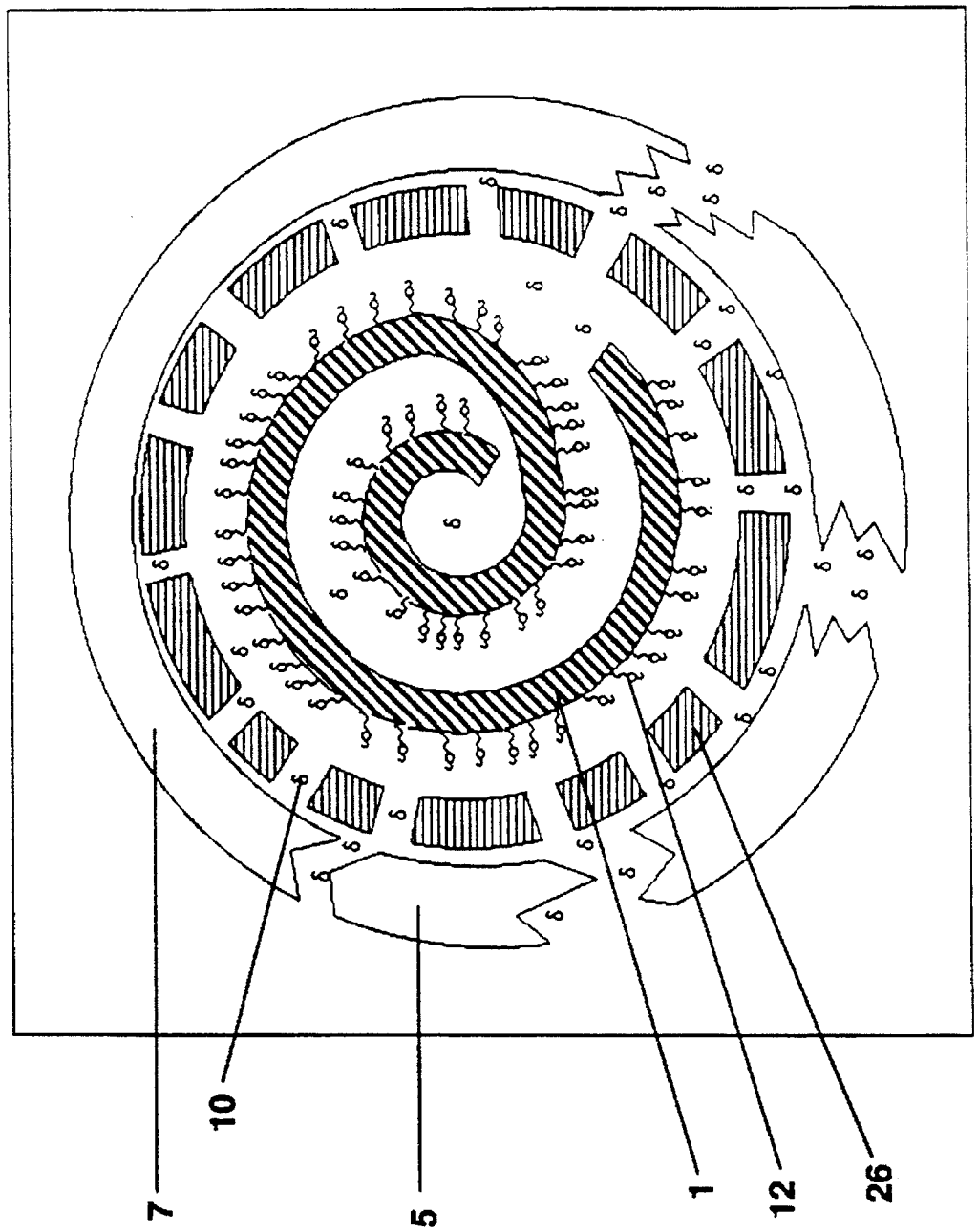
FIG. 5c This shows the invention placed within a fenestrated intramedullary rod. In this example, the medicine is free to diffuse into the interfragmentary space via holes in the IM rod.

The invention augments the function of and decreases the adverse effects of existing classes of fixation devices:

FIG. 5c depicts the invention after being treated with medicine and placed within a fenestrated IM rod, 26. When IM fixation of a fracture is required, a surgeon can use a fenestrated rod into which he/she can deploy the invention. In this embodiment, the patient can realize the benefits of rigid fixation and still enjoy the faster healing and fewer complications provided by this invention. Moreover, by delivering the device in this way one can, for the first time, deliver medicines directly, preferentially and in a timed-release fashion to the fracture without exposing the outside of the fracture. By augmenting the function of existing classes of devices like the IM rod, the fracture not only heals faster and with a better cosmetic and functional result, but this invention decreases the incidence of infection by permitting earlier removal of the rod from the fracture site. Surgical implementation of this invention is simple, keeping operating time and intraoperative morbidity to a minimum.

Figure 5D:
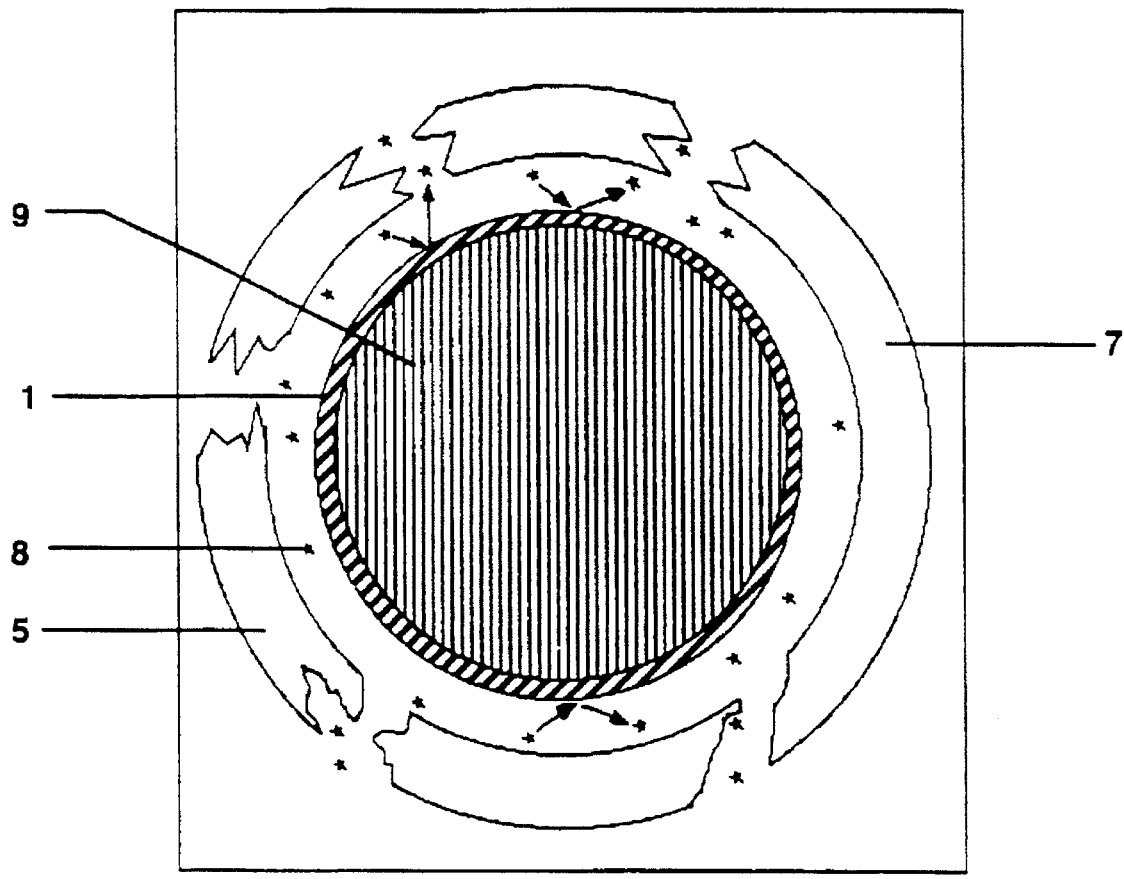
FIG. 5d In this embodiment, the macromolecular containment means of the device are being used to hinder bone formation on the rod. Note that the invention serves to restrain macromolecules produced by the fracture from interstices in the metal thereby providing for easier removal of the rod.

This invention can also be applied as a thin film to the surface of a solid rod, 9, before placing it (FIG. 5d). In this embodiment, one can not only contain macromolecules at the fracture site and deliver medicines directly and preferentially to the fracture, but by directing macromolecules back into the fracture and away from the rod, one achieves the unexpected benefit of inhibiting bony bridging between the fracture and the prosthetic, allowing easier removal of the rod.

Finger fractures are currently treated with Kirshner wires ("K" wires) that are applied percutaneously under local anesthesia. The K-wire is a solid, rigid wire that functions much like an intramedullary rod. Although not rigid like a K-wire, this invention can be applied like one using a hollow needle, and subsequently used to provide healing support to small bones. This invention can also be rolled up and delivered arthroscopically to treat cartilage and tendons.

Figure 6A:
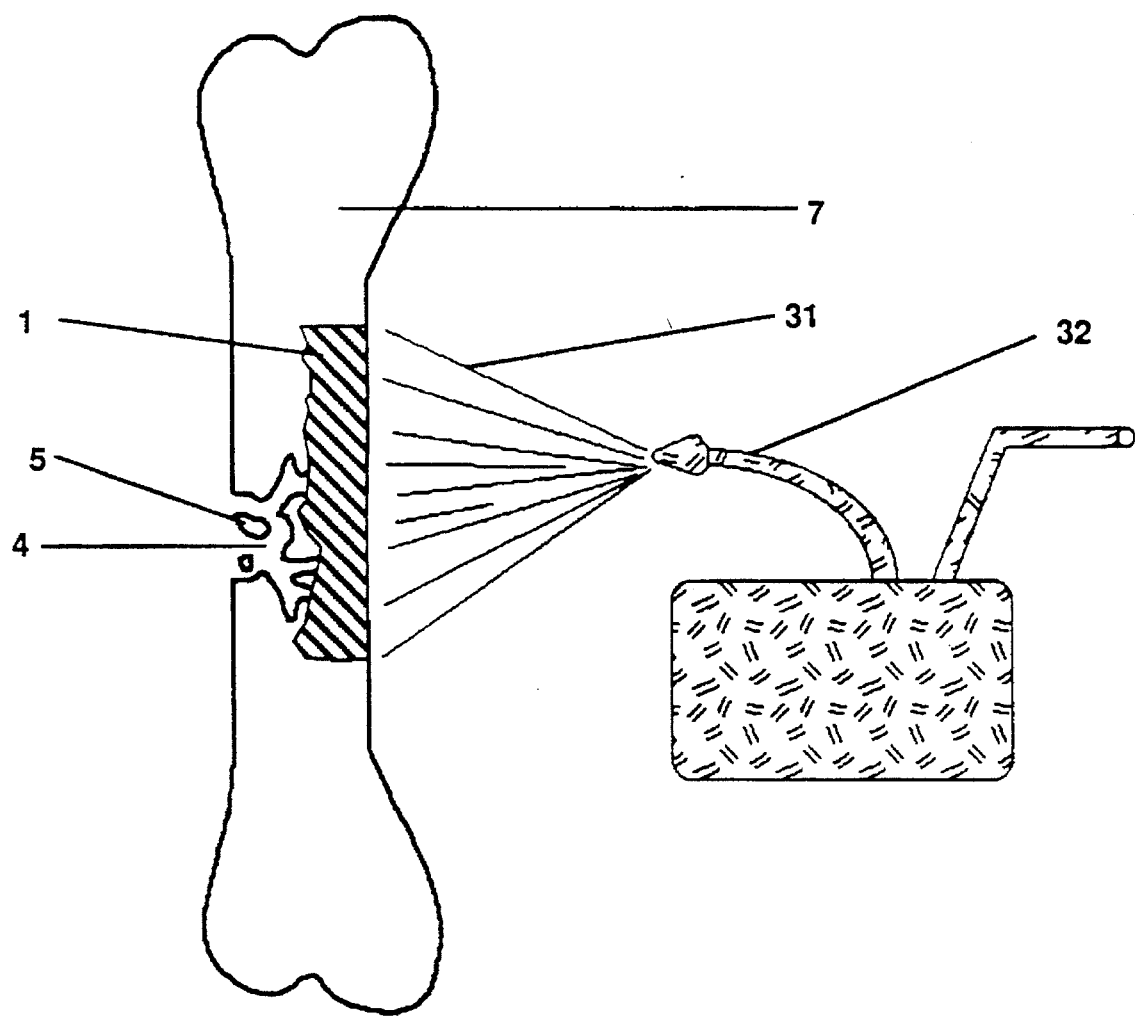
FIG. 6a In this example, the invention is being applied to a fractured bone as a spray.
Figure 6B:
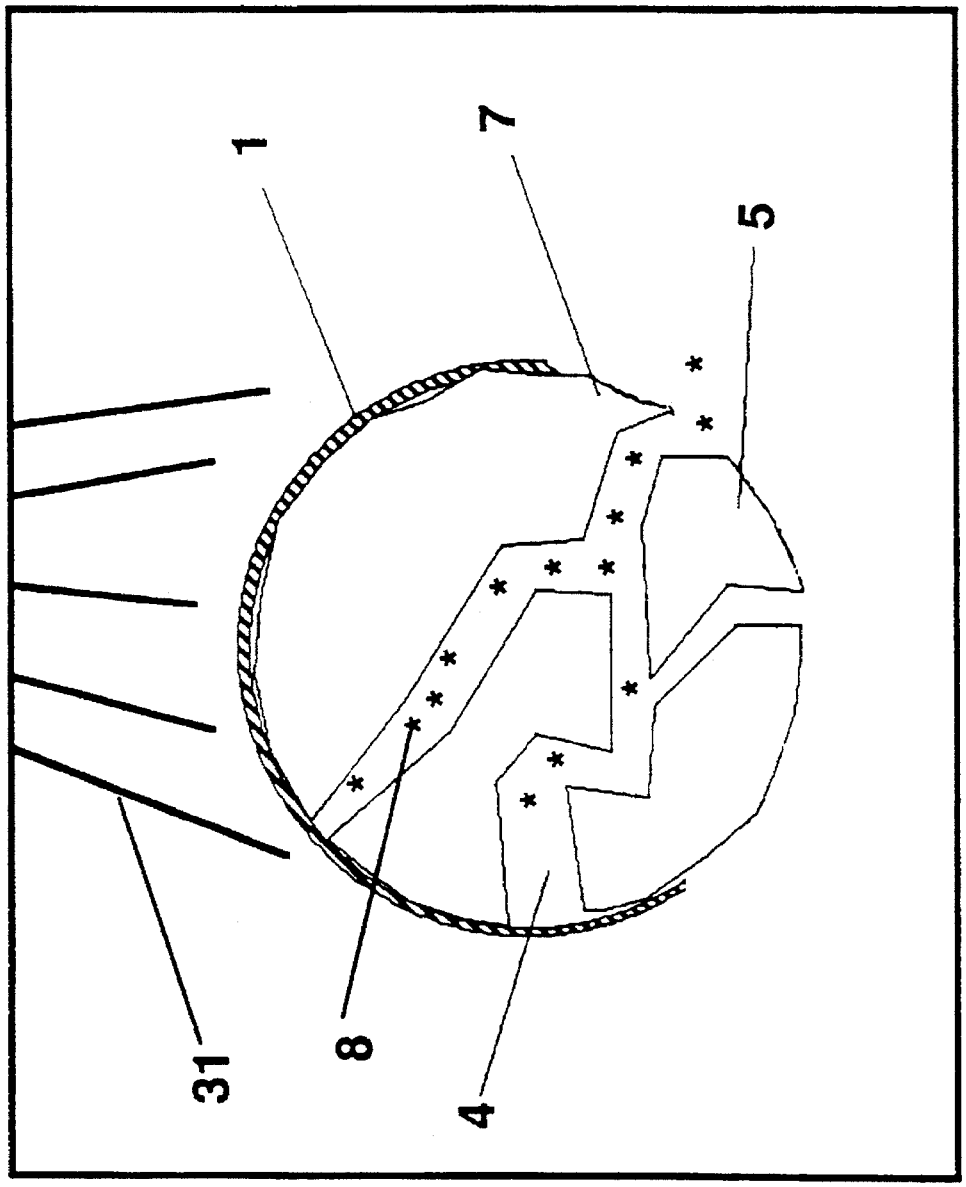
FIG. 6b This is a cross section of the site of injury after spray application of the invention. Note that in this method, the space between the injured tissue and the invention is minimized because the spray can follow the contour of the injury very closely.

Deployment of this invention as a spray:

Surprisingly, the invention can be applied to the site of injury as a spray, 31, such that it is deposited in a thin film on the tissue not unlike spray paint as shown in FIG. 6a and FIG. 6b. In this embodiment, the surgeon would expose the fracture, appose and align the fragments, and then from a spray can or reservoir, 32, spray the device on in a thick coat not unlike a silicone spray. The intimate association between the sprayed-on device, 1, and the bone dramatically decreases the space normally present at the device-bone interface. Consequently one can increase even more the concentration gradient between the interfragmentary space and the outside. As the polymer returns to a rubbery consistency, the surgeon need only cut or mold the device to meet the particular needs at the time. One can subsequently pass a needle through the device and load the interfragmentary space with medicine. Thus, the present invention can be used by the surgeon to maximize the surface area being treated while minimizing the need to dissect and staple.

The invention as a method and apparatus for percutaneous use

One of the most significant advances in modern medical care is the development of percutaneous therapies. Percutaneous procedures are done under local rather then general anesthesia, and are accomplished through small holes in the skin. Through these holes, the surgeon manipulates catheters and needles within hollow viscera and/or blood vessels to achieve the desired result. Percutaneous treatments markedly decrease hospital stays, and can turn what was once a several day in-hospital recovery period into an outpatient procedure.

Although not critically important for the subcutaneous introduction of devices, physicians almost universally agree that the smaller the introducer system the better. Because introducer systems need to be passed into blood vessels, the smaller they are the less chance for vessel damage and bleeding. Furthermore, the smaller the catheter system, the tighter radius of turn can be negotiated within a vessel lumen. Although the Malleable Fracture Stabilization Device with Micropores can be delivered percutaneously, the thinner design of the present invention is a significant improvement because the size of the introducer system can be markedly reduced.

Percutaneous treatment of bone pathology:

I have found unexpectedly that if I manufacture this invention as a sheet on the order of 200 microns thick, it can be rolled up and placed into a large-bore biopsy needle and advanced into the medullary cavity of a bone. If the device is made even thinner, it can be passed into blood vessels, 39, or other hollow organ or viscera, 38. Depending how thin one makes the minimally-porous sheet, one can deploy it percutaneously via introducer needles or via small rubber catheters. In fact, with the exception of the precoated IM rod shown in FIG. 5d, the intramedullary applications discussed in the above paragraphs can all be deployed percutaneously using an introducer needle, 48, which has been passed into the medullary canal. If one has trouble fully unrolling the device so to touch the inner bone surface, a balloon catheter, 37, can be passed through the vertex of the roll and inflated.

This device can be placed adjacent to herniated disks and provide local treatment both to the disk itself and to the inflammatory reaction in the surrounding nerve roots. Remarkably, one can also percutaneously deploy this invention along the external surface of a bone, if one uses x-ray guidance to wedge it between attached muscles and tendons.

One can also treat metabolic conditions such as osteoporosis locally by introducing this invention either within the medullary cavity or adjacent to the periosteum in areas high risk for fracture. One would simply need to direct the medication coated side appropriately. This technique can provide rapid, directed therapy to areas of high risk for fracture without need for operation. Moreover, because the device has macromolecular containment means, if medicines are injected into the space between the device and the bone they will stay there, allowing one to use a minimum of what is currently an expensive drug.

Because this invention embodies the unique combination of flexibility, thinness, and directional delivery capability, the percutaneous treatment of metastatic lesions, infections and even some metabolic disorders is now possible. This capability represents a major advance over prior art fixation devices because percutaneous, non-operative treatment of extremely sick patients like cancer patients may be their only chance for treatment at all.

Figure 7A:
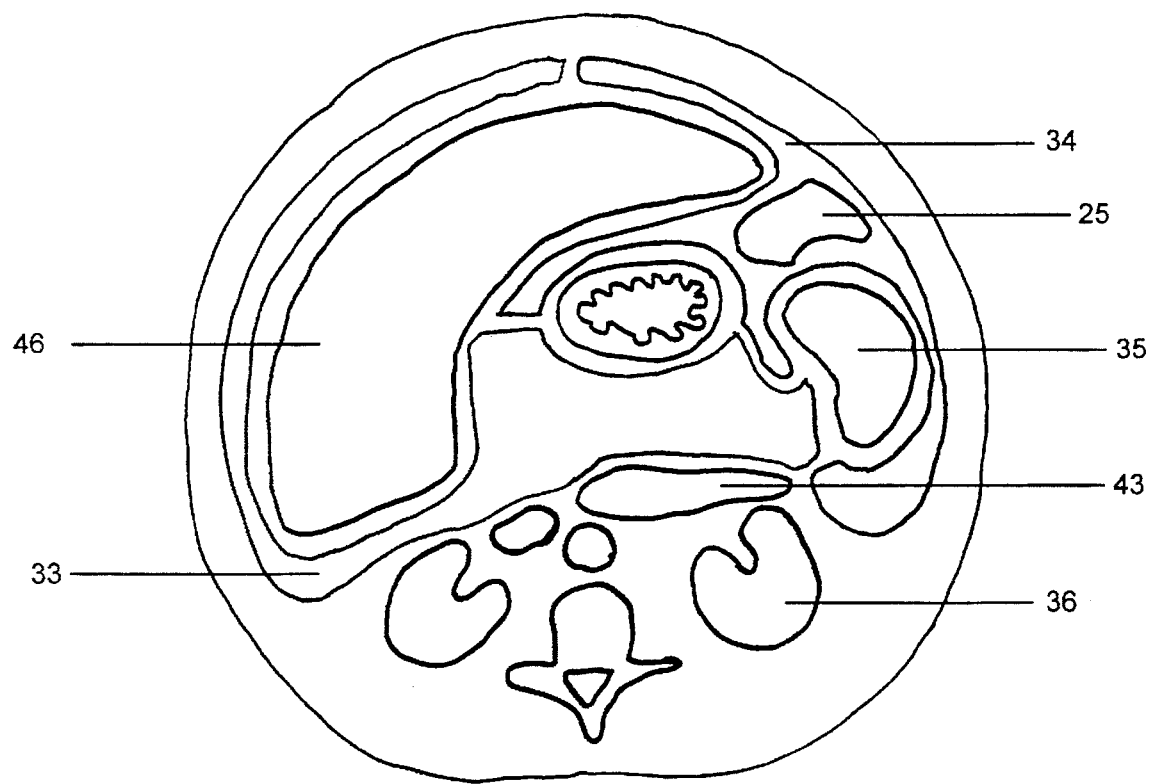
FIG. 7a This is an axial section taken through the mid abdomen of a human patient. In this example, the patient has an abscess within the greater sac between the liver and the spleen.
Figure 7B:
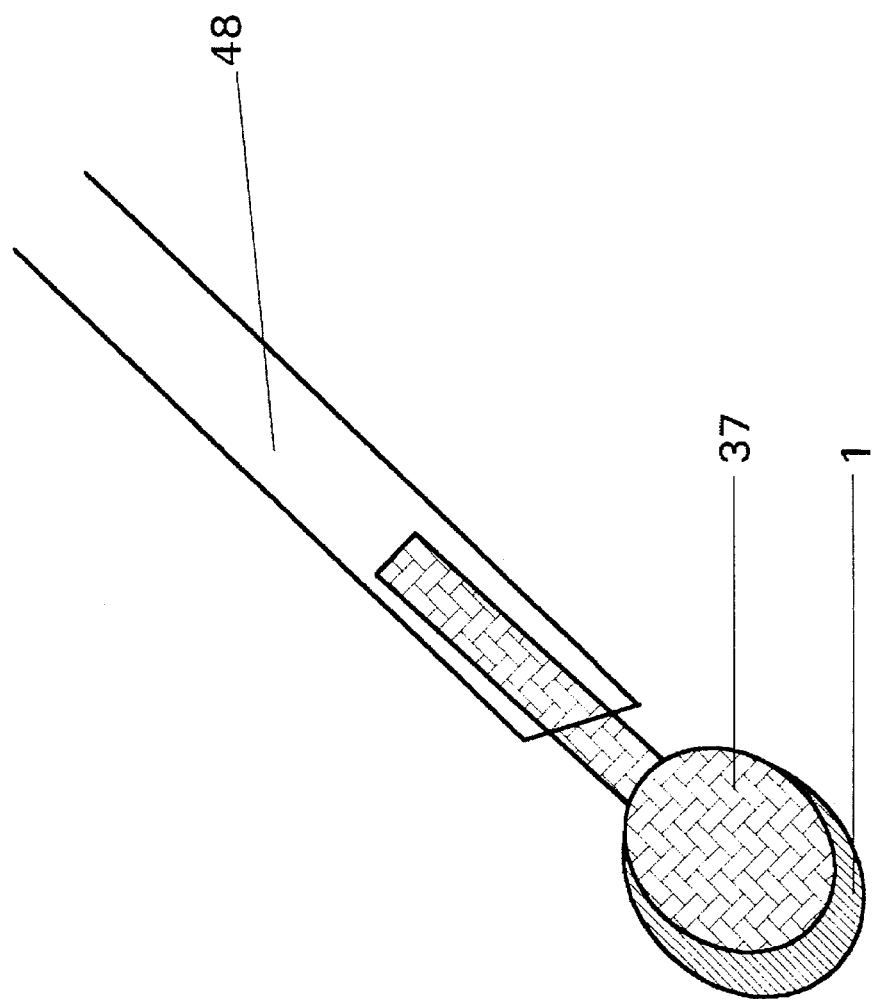
FIG. 7b This depicts the invention as it is being deployed over a balloon using a needle as an introducer system. In this case, the balloon is used to expand the rolled up device so it will become directly apposed to the abscess wall.

Percutaneous treatment of abscesses and contained soft tissue infections:

One of the most common serious complication of diverticulitis and inflammatory bowel disease is the formation of intraabdominal abscesses, 25. FIG. 7a depicts an abscess within the "greater sac", 34 of the abdomen. The lesser sac, 33, the spleen, 35, the liver, 46, the pancreas, 43, and the kidney, 36, are also shown for orientation. Fifteen years ago, this collection would have required open surgical drainage for adequate treatment; however in 1995, this drainage can be done percutaneously under CT guidance. One can use this invention to treat localized fluid collections such as these by introducing the device around an inflatable balloon as is shown in FIG. 7b. The ability to deploy this device around a balloon has several benefits.

Figure 7C:
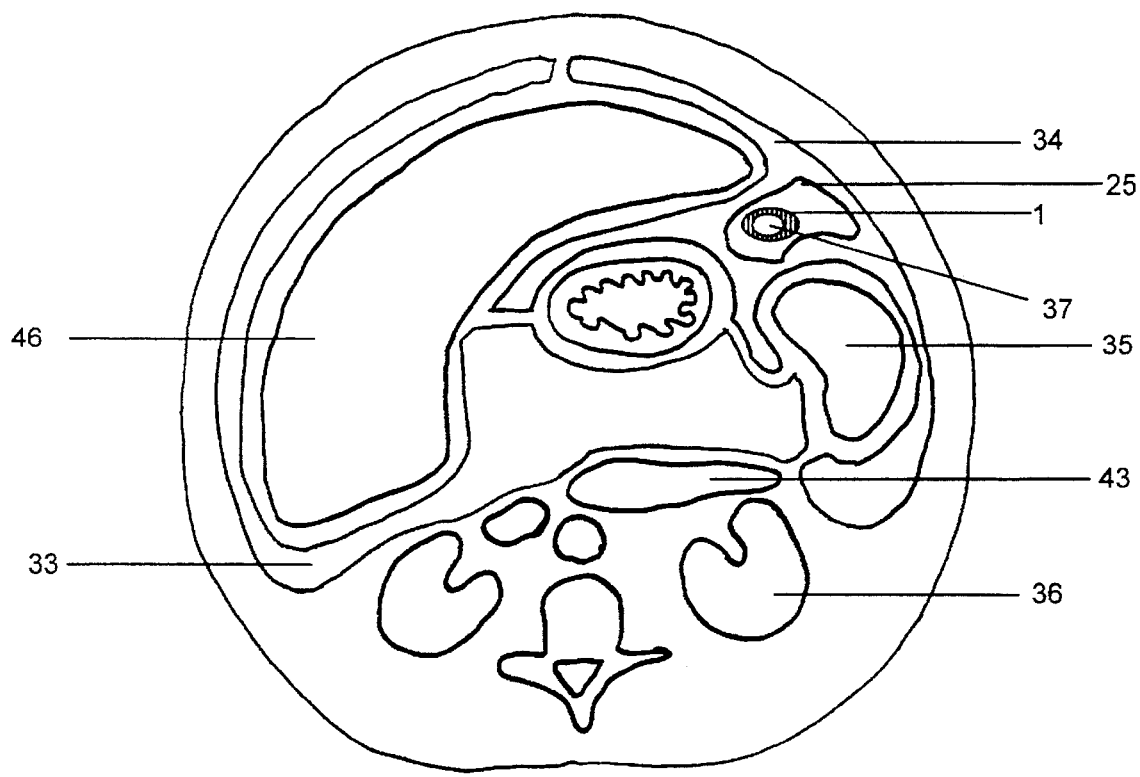
FIG. 7c This is a view of the abscess shown in FIG. 7a after the invention has been deployed within it. In this instance, the balloon has been detached within the abscess surrounded by the invention. Both the balloon and the invention can be made of resorbable polymers to eliminate the need for removal.

One can package the collapsed device inside a catheter system and deliver the invention at distant site. Once the device is pushed out of the introducer system, the three dimensional flexibility of the device will permit it to become intimately associated with small crevices of the lesion simply by expanding the collapsed invention with an inflatable balloon, 37, (FIG. 7c). In this way, antibiotics or other medicines can be delivered in a directional manner right at the site of the most active tissue destruction. The balloon can be removed once the device is deployed, or left in place to insure that the invention maintains its shape. If one deploys this invention made with a resorbable material, a surgeon needs only to deploy the device and allow it to dissolve as the patient heals. This method can also be used in the treatment of cystic tumors and aneurysms.

Percutaneous treatment of vascular disease:

A leading hypothesis to explain atherosclorotic plaque formation is that plaques form in response to repeated local trauma to the vessel wall. Hypertension or turbulence within the lumen causes tiny tears in the intimal lining of the vessel. When the vessel attempts to heal, neighboring cells of the intima elaborate a series of macromolecules to "patch" the defect. If the macromolecules are not kept substantially in place, they will be swept away by moving blood. The injured cells must then secrete more and more macromolecules to keep up with the loss. Meanwhile, the injury keeps getting larger and larger. It follows that the sooner the injury is repaired, the smaller the resulting plaque will be.

Figure 8A:
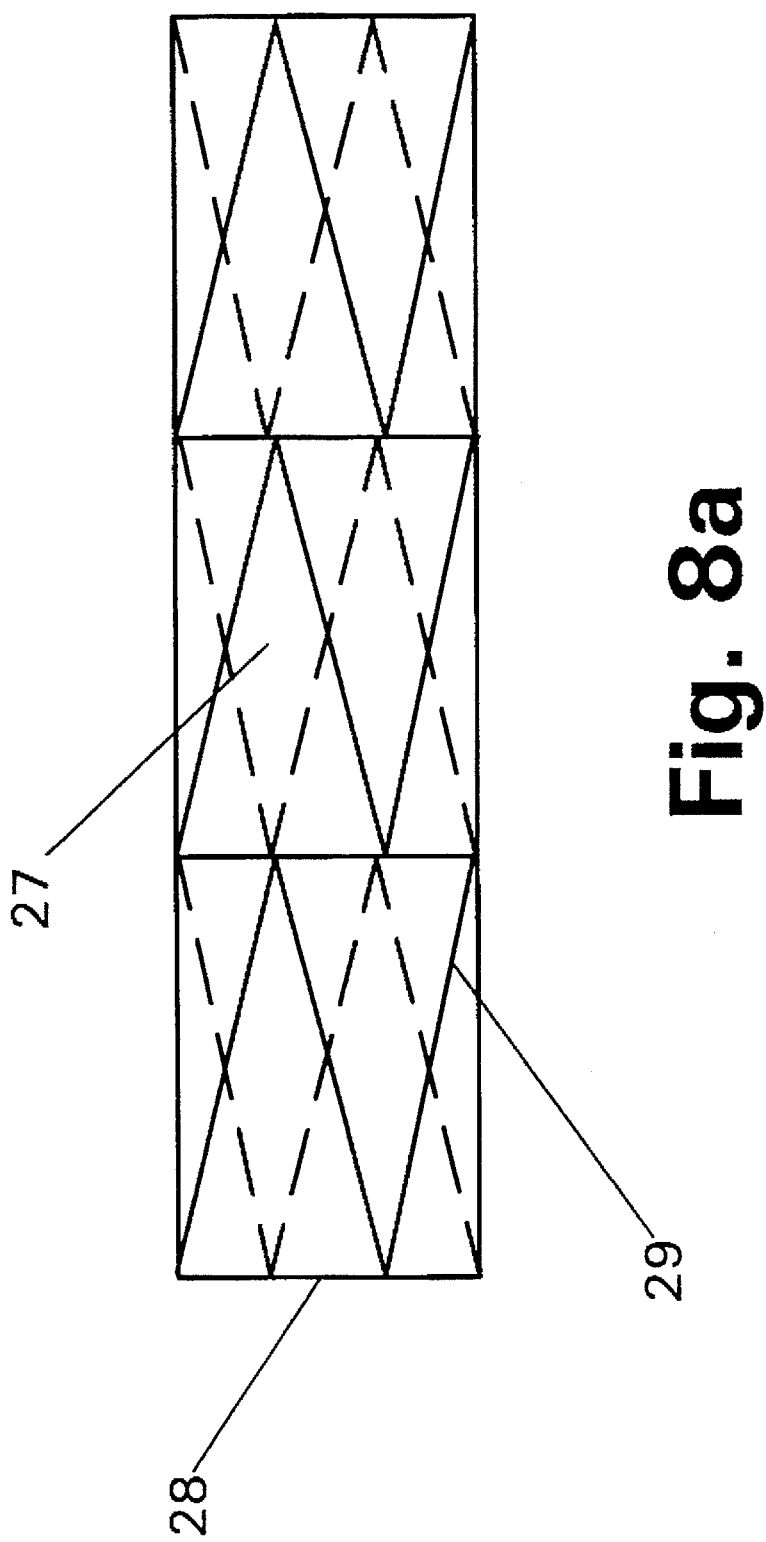
FIG. 8a Side view of a currently-used expandable stent, the Gianturco-Rosch COOK-Z™ stent (prior art)
Figure 8B:
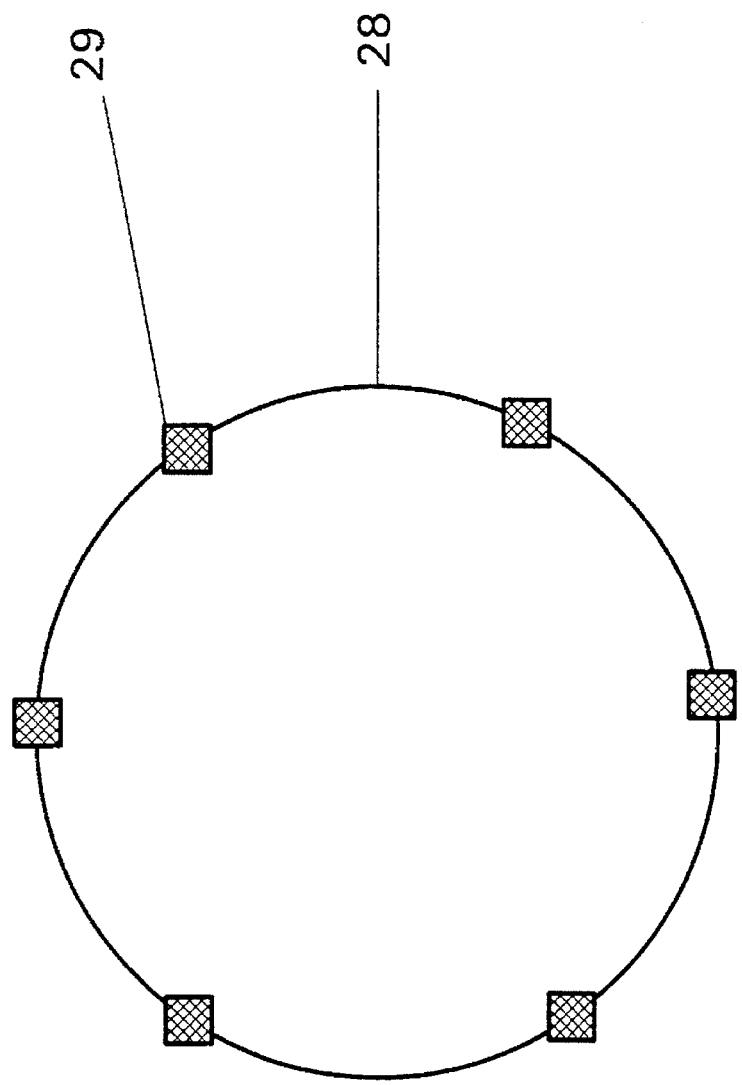
FIG. 8b End on view of the Gianturco-Rosch COOK-Z™ stent (prior art)
Figure 8C:
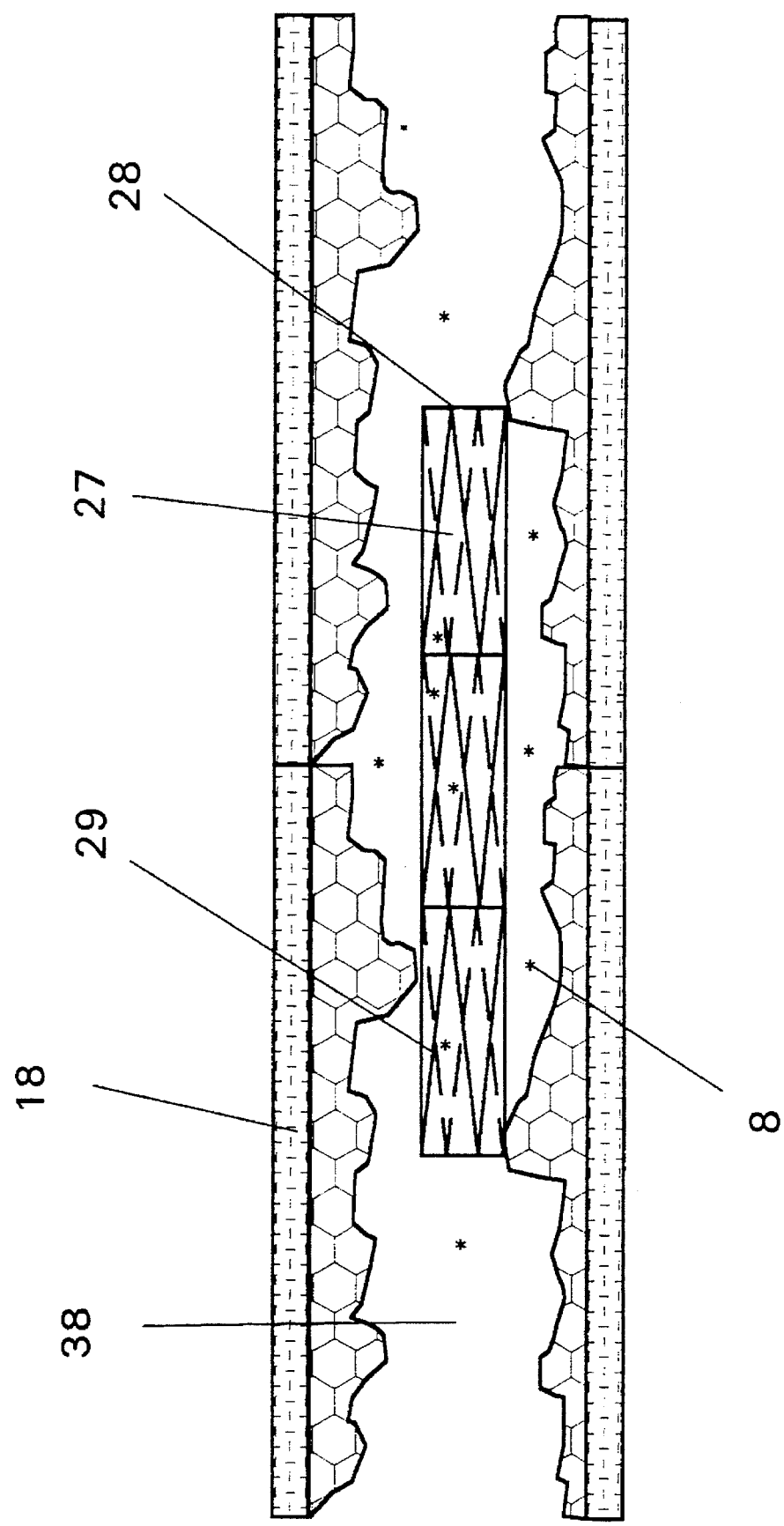
FIG. 8c View of a atherosclorotic blood vessel before ("A") and after ("B") deployment of a Gianturco-Rosch COOK-Z™ stent FIG. 8d View of the stent sheath of Scott et al (prior art, U.S. Pat No. 5,383,928)

Current vascular stents are porous meshes made of either metal, e.g., Gianturco-Rosch COOK-Z™ stent (FIGS. 8a and 8b) and the Wallstent™, or made of plastic. The Gianturco-Rosch COOK-Z™ stent parts, i.e., the support strut, 29, and support ring, 28, are shown. Plastic stents are of limited use in vascular diseases because they are very difficult to make thin enough for small catheter delivery; however the metallic stents are in widespread use. FIG. 8c depicts a cross section of a blood vessel wall, 39, with a large atherosclerotic plaque, 18, and the same vessel after placement of a Gianturco-Rosch COOK-Z™ stent. The lumen of the blood vessel is also shown, 38.

Figure 8D:
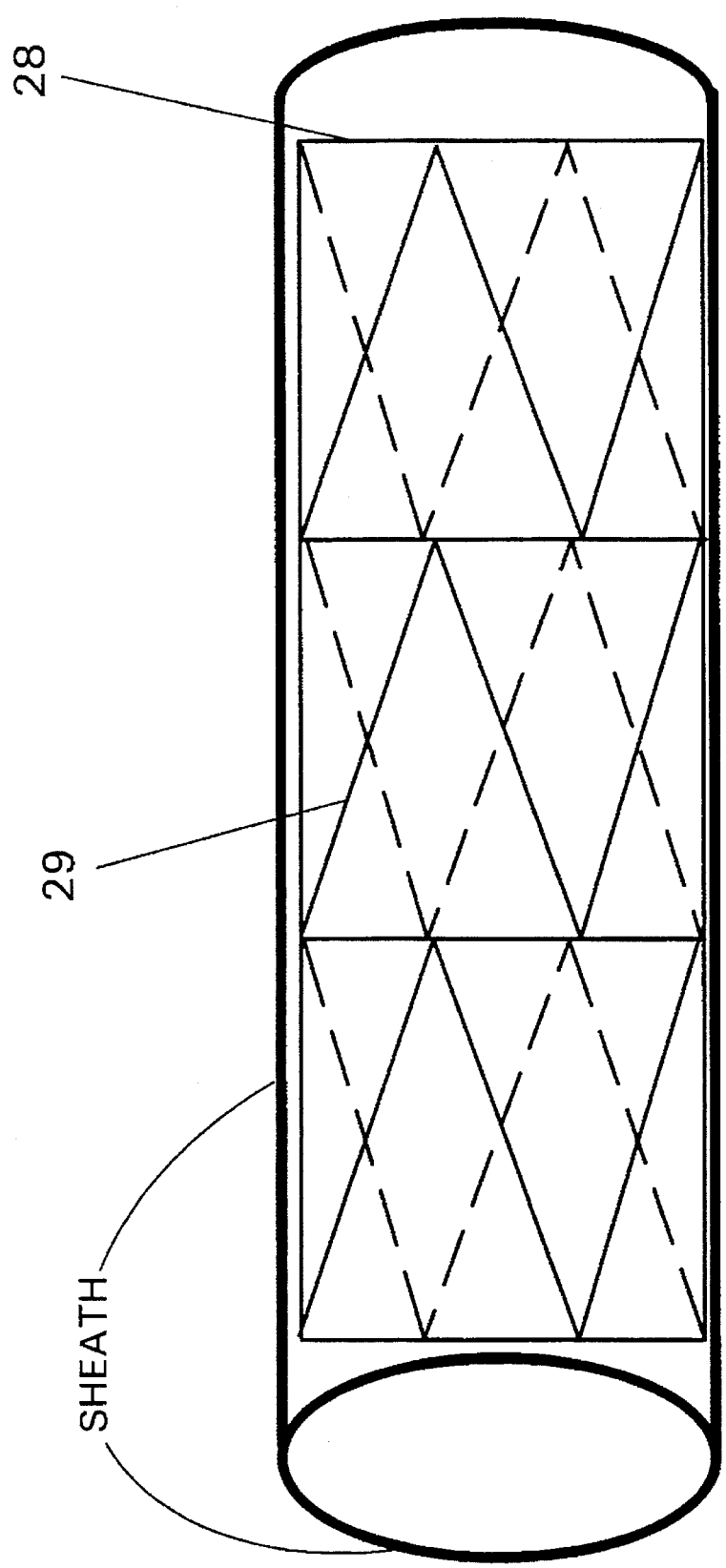

Both the Gianturco-Rosch COOK-Z™ stent and the Wallstent are designed expandable and the mesh holes, 27, open when they are deployed. Because the smallest holes are tens of microns in diameter, both cells and large macromolecules are free to move through them. A very recent improvement on this design has been disclosed by Scott et al in U.S. Pat. No. 5,383,928 (FIG. 8d). These authors propose a stent sheath that can cover the metallic mesh of a porous stent thereby somewhat limiting its porosity. These authors have also disclosed an improvement in their sheath describing how medicine can be imbedded in this sheath for local delivery.

The work of Scott et al. represents a significant advance; however their stent sheath does not have means to restrain macromolecules between their sheath and the vessel wall. From the above discussion, the reader will note that the ability to restrain the macromolecules elaborated by the healing tissue is a exceedingly important feature. Furthermore, because their sheath does not restrain macromolecules, their sheath cannot have the "directional drug delivery means" necessary to restrain the medicine that their sheath delivers. For example, it would be highly undesirable to deliver an anti-clotting medicine to the outer surface of the stent where one needs a clot to form to secure the device.

Figure 8E:
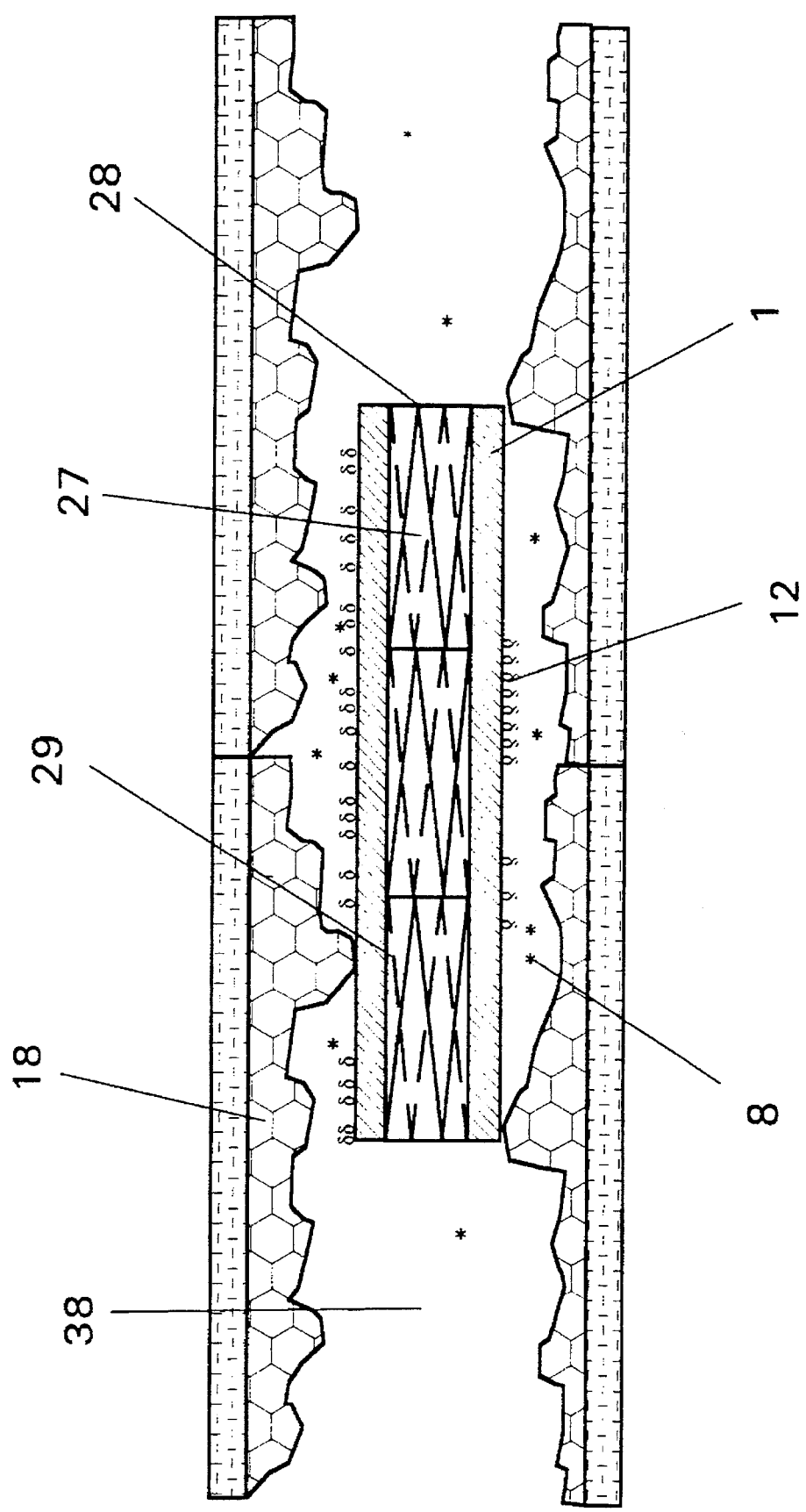
FIG. 8e Side view of the present invention wrapped around the Gianturco-Rosch COOK-Z™ stent and placed in the lumen of a blood vessel. This example shows unidirectional delivery of medicine from the outer surface taking advantage of the macromolecular containment means of the minimally-porous sheet.
Figure 8G:
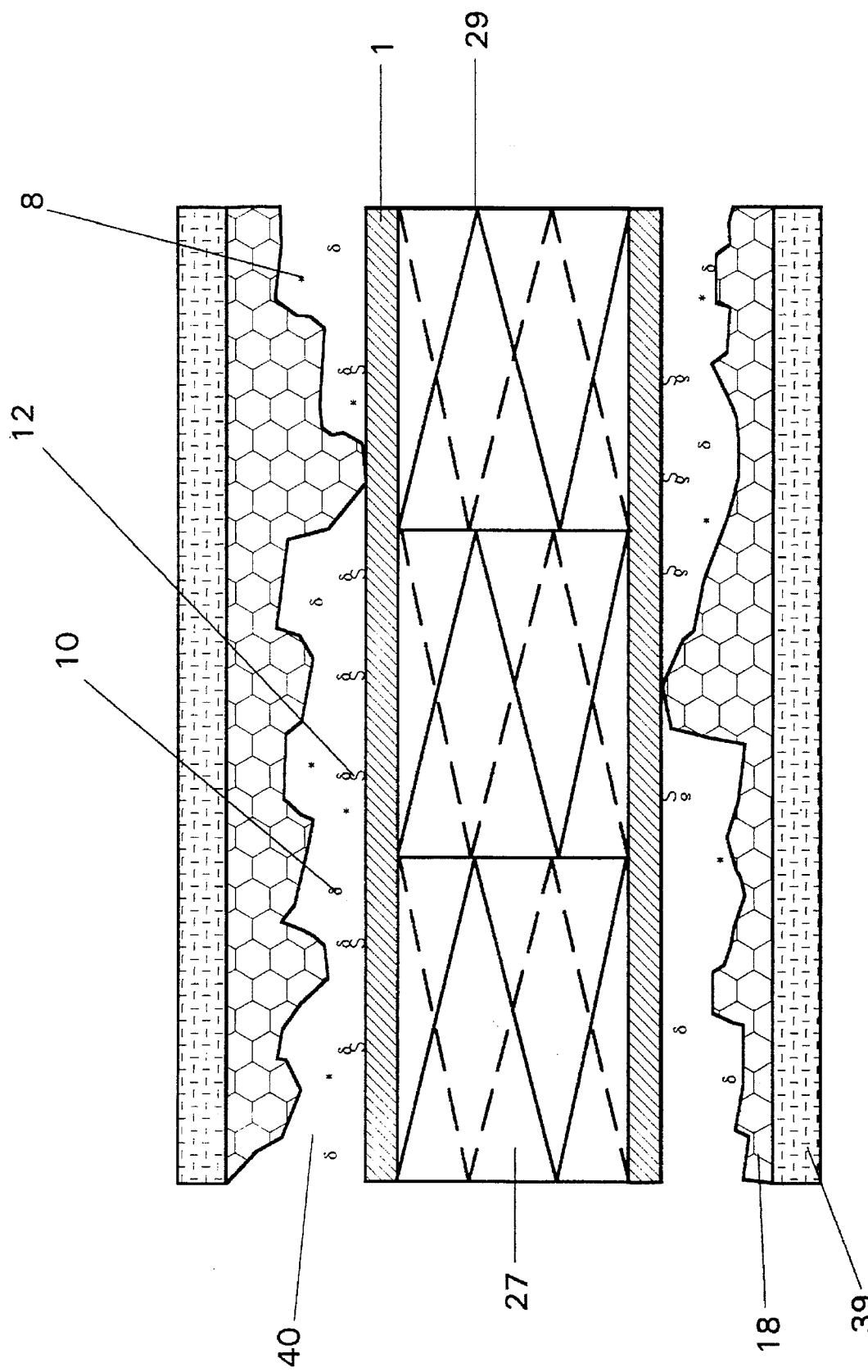
FIG. 8g This displays a magnified view of the interface between the atherosclorotic plaque and the invention. Note that both the macromolecules produced by the abnormal tissue and the treating material are contained within the interstices of the plaque by the macromolecular restrainment means of the invention.
Figure 8H:
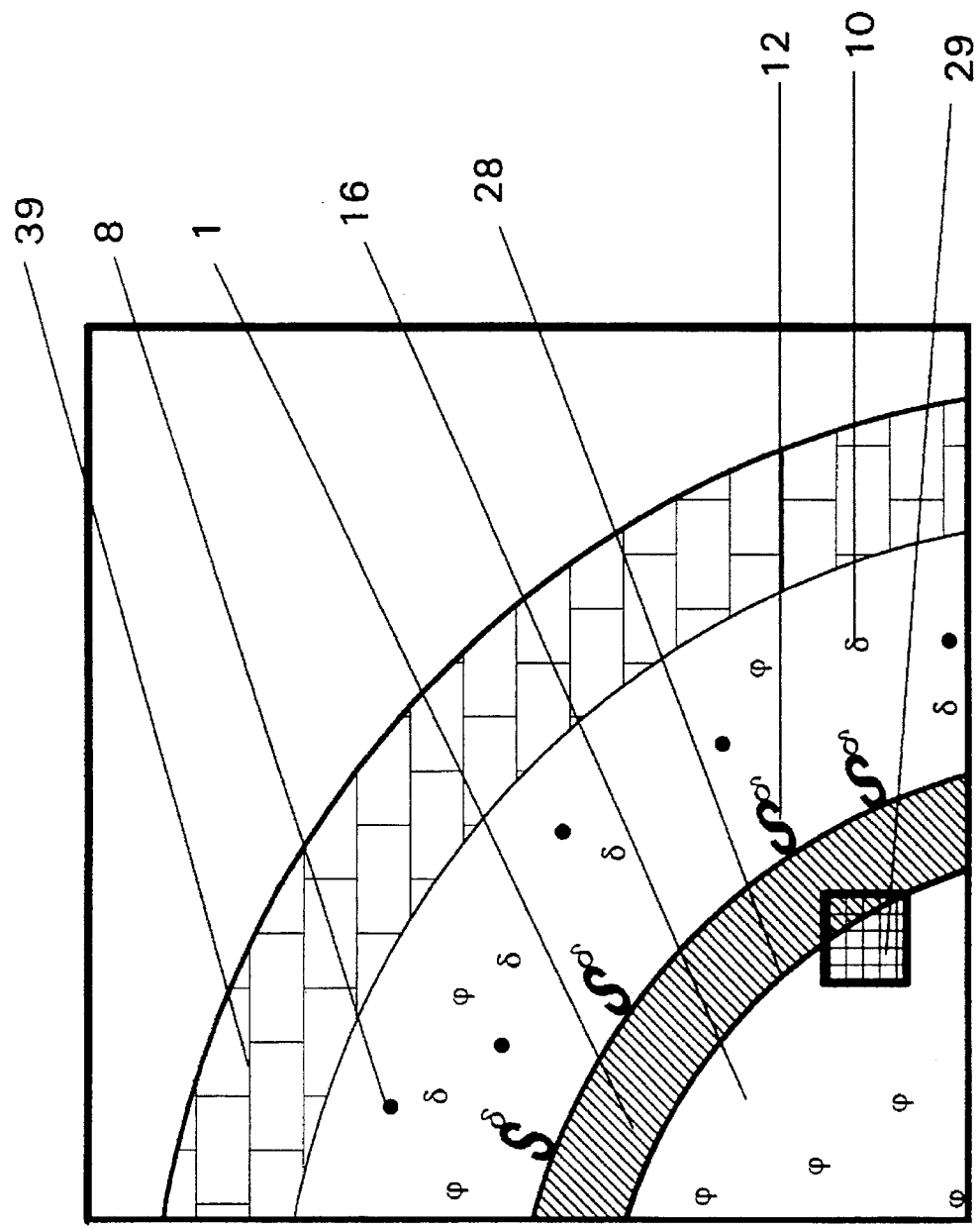

This invention provides the means to restrain the macromolecules elaborated by the healing tissue, as well as the ability to restrain any number of medicines in the space adjacent to the injured blood vessel wall, 40, (FIGS. 8e, 8f & 8g). Note that in all cases, small metabolites are free to pass through the invention into the lumen (FIG. 8h). The device can be manufactured with any stent, and depending on how thin the device is, can be delivered via catheter, needle, or open surgical procedure. The invention can also be used to treat mycotic aneurysms, i.e., aneurysms that are caused by an infection of the vessel wall, simply by using this device to which has been affixed an antibiotic.

Percutaneous treatment of endolumenal malignancies

Figure 9A:
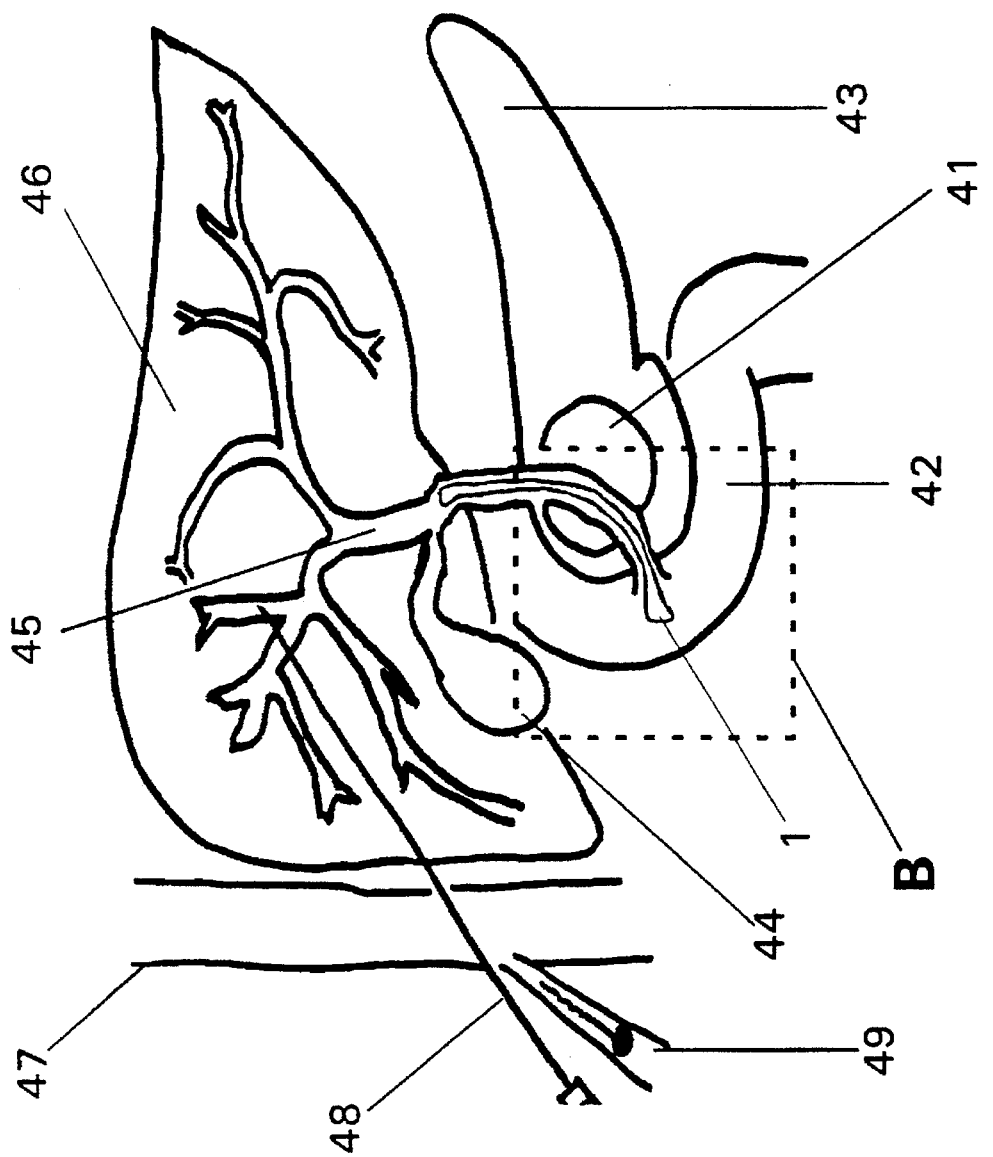
FIG. 9a This is a coronal representation of the human hepatobiliary system. In this embodiment, the device of the present invention has been wrapped around a stent in much the same way as is shown in FIG. 8d. Note that the covered stent is placed within the common bile duct bridging and immediately adjacent to a malignant stricture caused by a tumor in the head of the pancreas. The dashed box, "B", is magnified in FIG. 9b.
Figure 9B:
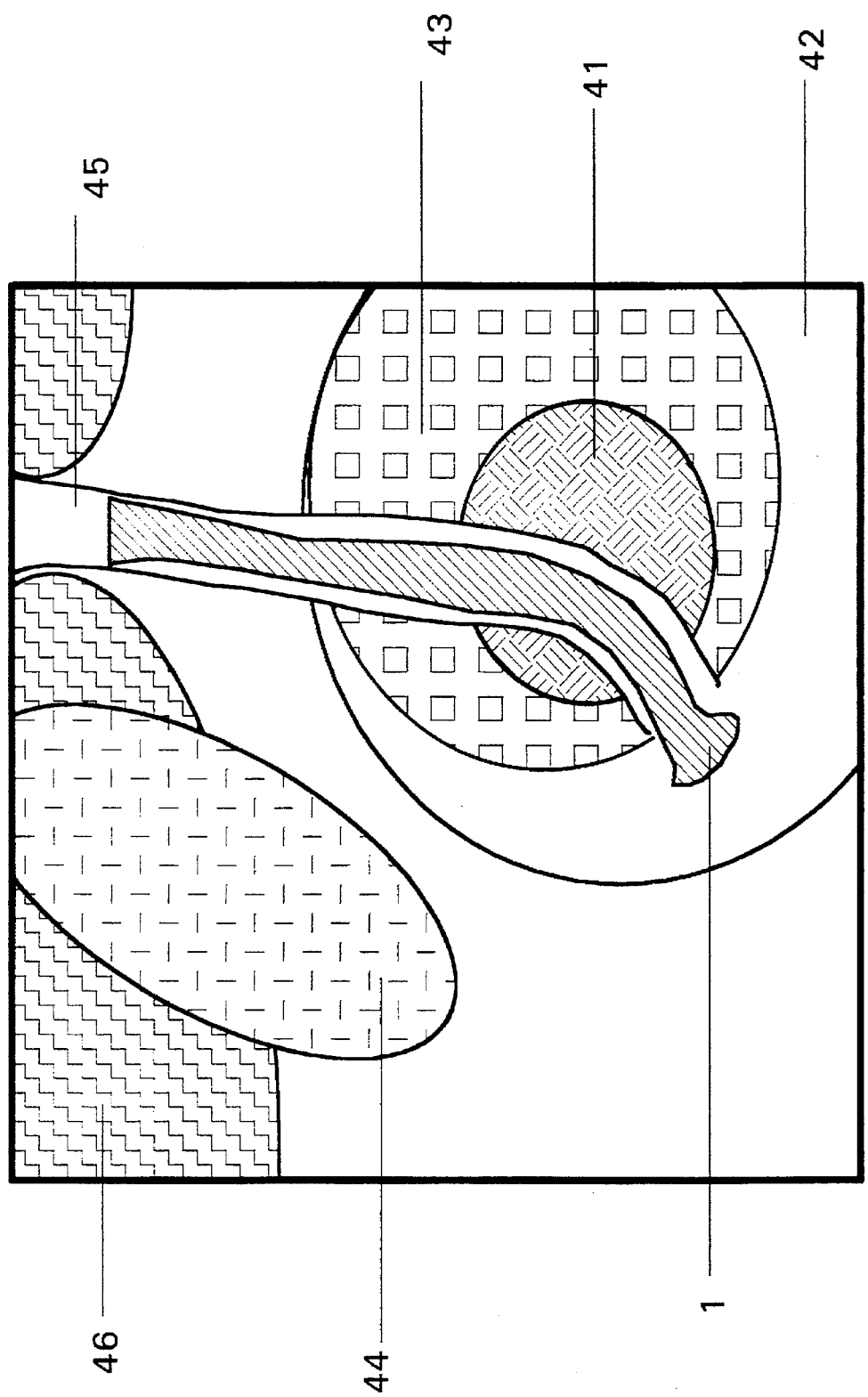
FIG. 9b This magnified view of the boxed area "B" shown in FIG. 9a illustrates a typical placement of a stent wrapped by the invention.

The stent coating properties of this device are not limited to use within the vascular system. One can use an invention-coated Wallstent within the biliary system or esophagus just as easily. FIGS. 9a–b show this invention being used to coat a stent in the common bile duct, 45, that has been placed to relieve a malignant biliary stricture caused by a pancreatic head tumor, 41. The gallbladder, 44, duodenum, 42, skin, 47, and Kelley clamp, 49, are shown for orientation. The principles of use in hollow viscera are virtually the same as within the vasculature, with a few important exceptions.

Biliary stents fail largely for two reasons. First, macromolecules and debris elaborated by the tumor coalesce within the stent lumen and subsequently clog it up. When the stent becomes obstructed and the bile gets infected, biliary sepsis results and a team must be called in emergently to decompress it. In fact, the reason many patients die from pancreatic cancer is from biliary sepsis. Second, malignant cells can overgrow the stent and subsequently obstruct either the inflow or the outflow.

Figure 9C:
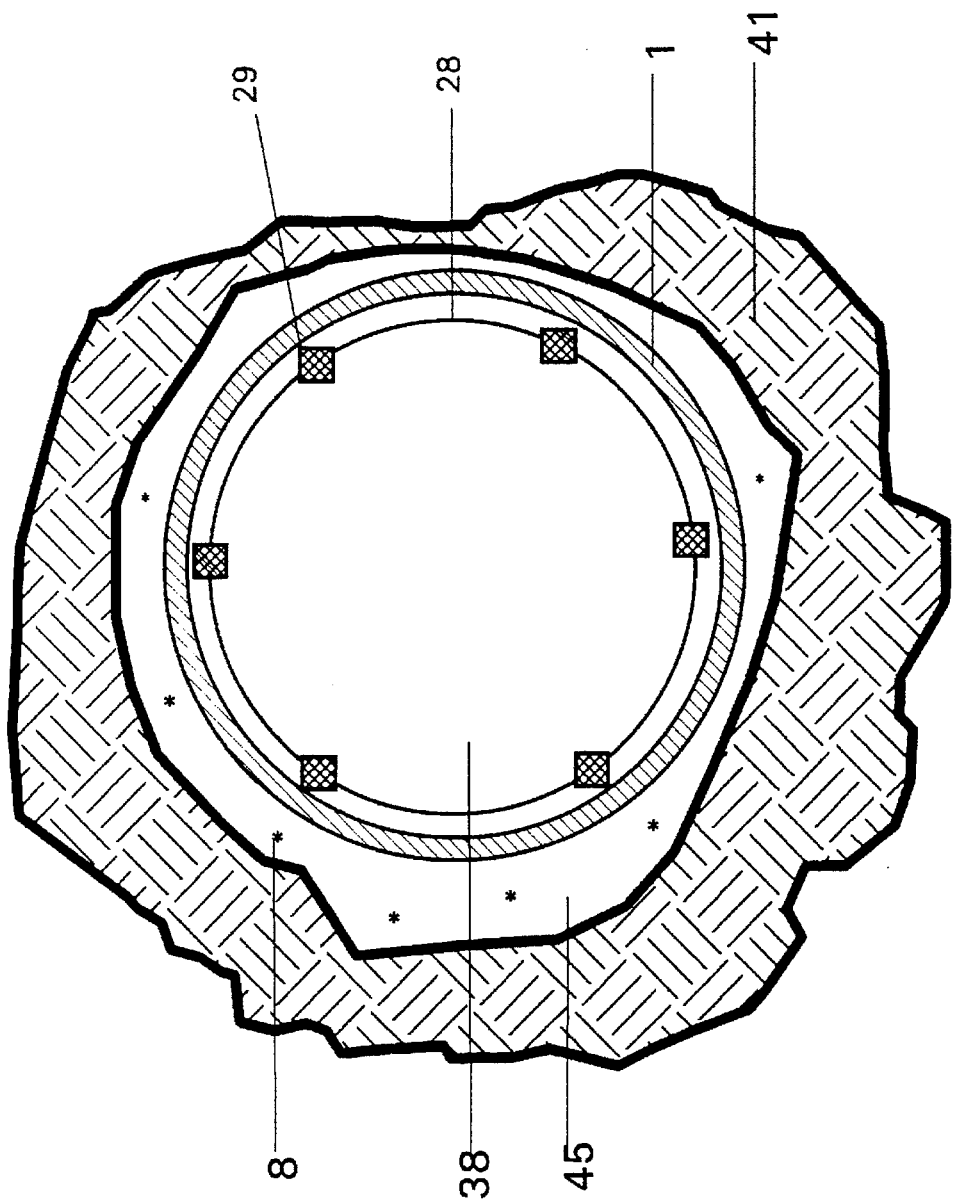
FIG. 9c This drawing shows the invention placed in a malignant biliary stricture. Note that the macromolecular restrainment means not only restrains macromolecules and cells produced by the tumor but also prevents debris from clogging the lumen of the stent.
Figure 9D:
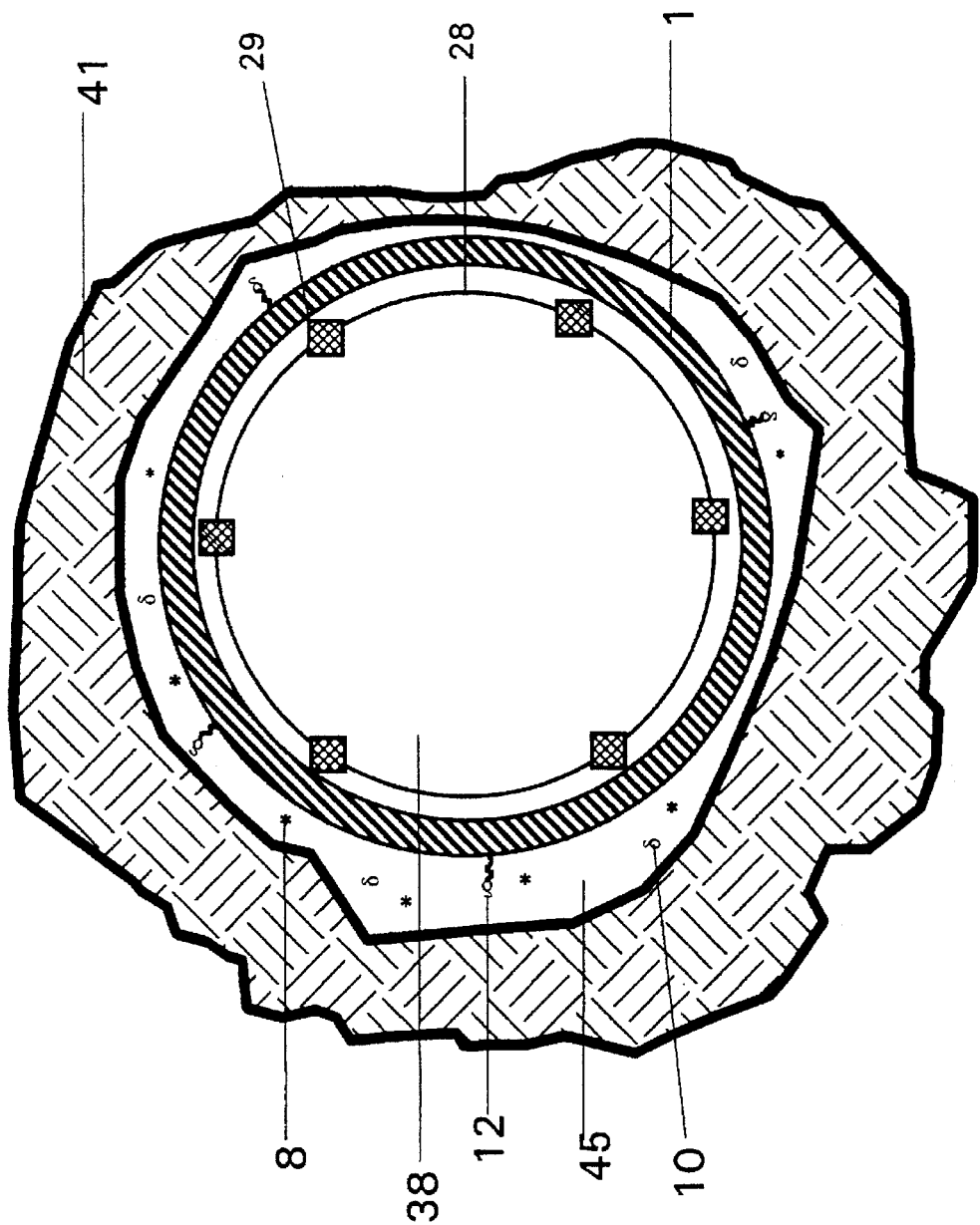
FIG. 9d This drawing shows the invention placed in a malignant biliary stricture with the medicine-coated side directed out. Note that as the macromolecular restrainment means prevents debris from clogging the stent, medicine is delivered locally to the tumor. The entire length of the device covering the stent need not be coated with medicine for it to be efficacious, but the region of the device adjacent to the tumor should be to achieve maximum benefit.

When this device is used to coat a biliary stent, there results a significantly lower clog rate than currently used stents for two main reasons. First, this device capable of substantially restricting the flow of macromolecules elaborated by the tumor into the lumen. The invention is capable of restraining the tumor proteins long enough for them to be substantially broken down in the space between the device and the tumor instead of polymerizing within the lumen causing clogging (FIG. 9c). Second, when a chemotheraputic agent is affixed to the device, local anti metabolic therapy can be administered to combat the most aggressive cells (FIG. 9d). Since the fast growing cells are the ones that clog the stent, this device can be used to deliver drugs directly to the area where it is needed most.

Figure 9E:
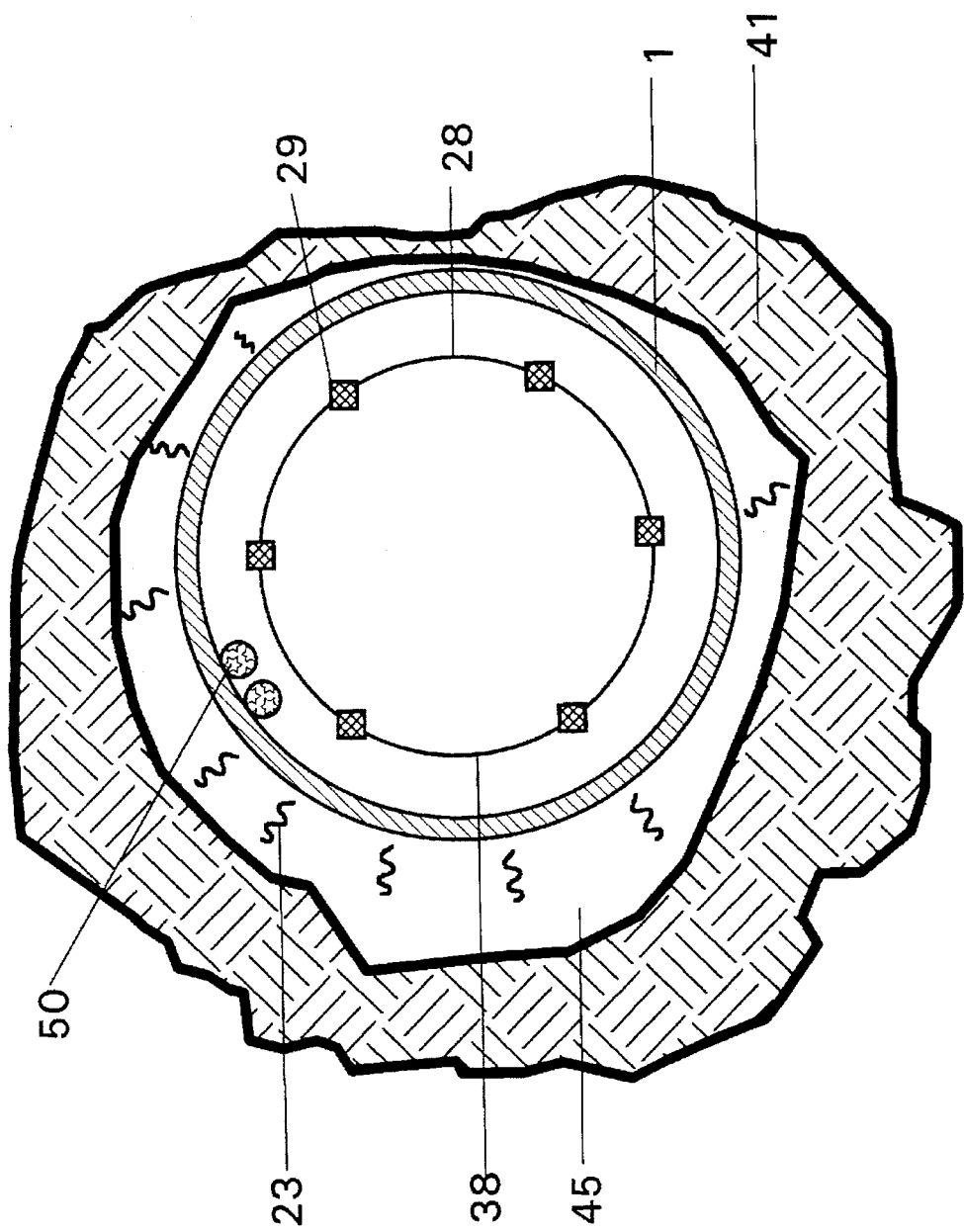
FIG. 9e This drawing also shows the invention placed in a malignant biliary stricture; however, instead of providing a coating of medicine, there is provided means to deliver energy directly and preferentially to the tumor. In this embodiment, there is provided a "energy sink" on the major surface that is facing away from the lesion. The wavy lines represent energy rather than a particular diffusable macromolecule.

The invention can also be used to deliver radiofrequency energy or radioactivity directly to the tumor. FIG. 9e also shows the invention placed in a malignant biliary stricture; however, instead of providing a coating of medicine, there is provided means to deliver energy directly and preferentially to the tumor. In this embodiment, there is provided an energy introducer conduit, 50, and an "energy sink", 15, on the major surface that is facing away from the lesion. The wavy lines represent energy, 23, rather than a particular diffusable macromolecule.

Ramifications and scope:

Accordingly, the reader will see that this device and the method of its use address the principal problem in healing serious bone fractures The efflux of growth promoting macromolecules from the interfragmentary space. This device and the method outlined above not only can substantially increase the rate of bony bridging between major and minor fracture fragments, but can also dramatically decrease the amount of heterotopic bone formation within the surrounding muscles. Surprisingly, this can be accomplished using a single layer of minimally-porous material wrapped around the fracture.

The ability to attain the healing power of the Malleable Fracture Stabilization Device with Micropores using a single sheet is a significant improvement in design because the device can now be made much thinner. The thinness of the device provides the unexpected ability to much more easily apply the healing benefits of the Malleable Fracture Stabilization Device with Micropores to the medullary canal, hollow organs, and blood vessels. The size of the device also permits, for the first time, the ability to add an energy sink layer so that one can deliver radiofrequency treatment directly and specifically to the surface of a lesion.

The rate of healing can be further accelerated by the attachment of a treating material, either mechanically or by chemical bond, to the inner surface of the device. The method of medicine release by chemical bond is also a highly significant improvement over the prior art. Prior art references all rely on the efflux of treating materials from micropores to deliver medicine. The ability to release medicine according to a rate constant, rather than relying on random efflux of molecules from various sized micropores, provide a surprising consistency to drug delivery not before seen in the art. Moreover, the chemical coupling of medicine and device provides for unprecedented specificity of release. The unexpected ability to be able to link medicine release with the specific enzymatic activity of healing cells is a highly significant improvement over the prior art.

As the reader can appreciate, the device and method provided is not only a major advance in bone fracture treatment over the prior art, but is also a significant advance in the treatment of other seemingly unrelated soft tissue pathology.

Thus the scope of the invention should be determined not only by the content of the above sections but also by the appended claims and their legal equivalents, rather than by the specific examples given.

Having described in detail the invention and some methods of its use, I claim:

1. A flexible fixation device for implantation into human or animal tissue to promote healing of a damaged tissue comprising:

a layer of flexible material that is minimally porous to macromolecules, said layer having a first and second major surface, the layer being capable of being shaped in three dimensions by manipulation by human hands, the first major surface of the layer being adapted to be placed adjacent to a damaged tissue, the second major surface of the layer being adapted to be placed opposite to the damaged tissue, the layer having material release means for release of an at least one treating material in a directional manner when said layer is placed adjacent to a damaged tissue, the device being flexible in three dimensions by manipulation by human hands, the device being capable of substantially restricting the through passage of at least one type of macromolecule therethrough.

2. The device of claim 1 wherein the at least one treating material is selected from the group consisting of a growth factor, extracellular matrix components, morphogenetic molecules, nerve growth factors, connective tissue growth factors, antibiotics, vitamins, cofactors, a glycosaminoglycan, proteins, a bioactive ion, nuclear or ionic radiation, radiofrequency, molecule produced by fractured tissue, a pharmaceutical, a hormone, and living cells.

3. The device of claim 1 whereby said layer is capable of release of the at least one treating material by lysis of a chemical bond.

4. The device of claim 1 whereby the apposition of the device adjacent to the damaged tissue forms a chamber, one wall of the chamber being formed by the layer, one wall of the chamber being formed by the damage tissue, such that the formed chamber contains a greater concentration of at least one type of macromolecule compared to outside the chamber.

5. The device of claim 1 whereby the apposition of the device adjacent to the damaged tissue forms a chamber, one wall of the chamber being formed by the layer, one wall of the chamber being formed by the damaged tissue, such that the formed chamber contains a lower concentration of at least one type of macromolecule compared to outside the chamber.

6. The device of claim 1 whereby the layer is capable of being affixed to a fixation device.

7. The device of claim 4 whereby the formed chamber is capable of containing the at least one treating material adjacent to a damaged tissue.

8. A method of treating a damaged tissue to promote repair comprising:

a) providing a device including, a layer of flexible material that is minimally porous to macromolecules, said layer having a first and second major surface, the layer being capable of shaping in three dimensions by manipulation by human hands, the first major surface of the layer being adapted to be placed adjacent to the damaged tissue, the second major surface of the layer being adapted to be placed opposite to the damaged tissue, the layer having material release means for release of an at least one treating material in a unidirectional manner when said layer is placed adjacent to the damaged tissue, the device being flexible in three dimensions by manipulation by human hands, the device being capable of restricting the through passage of at least one type of macromolecule therethrough, b) placing the device adjacent to a damaged tissue, c) whereby the placed device results in directional presentation of the at least one treating material.

9. The method of claim 8, whereby the layer permits the through passage of small molecules such that the device is non-toxic to the damaged tissue.

10. The method of claim 8, wherein molecules produced by the damaged tissue are substantially restricted adjacent to the damaged tissue.

11. The method of claim 8, wherein the at least one treating material is affixed to the layer prior to placement of the device adjacent to the damaged tissue.

12. The method of claim 8, wherein the at least one treating material is affixed to the layer after placement of the device adjacent to the damaged tissue.

13. The method of claim 8, whereby the layer is capable of being affixed to a fixation device prior to implantation of the device adjacent to the damaged tissue.

14. The method of claim 8, whereby the layer is capable of being affixed to a fixation device after implantation of the device adjacent to the damaged tissue.

15. A method of treating tissues in human or veterinary medicine comprising the steps of:

a) providing a device comprising, a layer of flexible material that is minimally porous to macromolecules, said layer having a first and second major surface, the layer being capable of shaping in three dimensions by manipulation by human hands, the first major surface of the layer being adapted to be placed adjacent to a damaged tissue, the second major surface of the layer being adapted to be placed opposite to the damaged tissue, the layer having material release means for release of an at least one treating material in a unidirectional manner, the device being flexible in three dimensions by manipulation by human hands, the device being capable of substantially restricting the through passage of at least one type of macromolecule therethrough;

b) placing the device adjacent to a tissue c) whereby the placed device permits directional presentation of the at least one treating material.

16. The method of claim 15 wherein the placed device substantially restrains at least one type of macromolecule produced by adjacent tissue.

17. The method of claim 15 whereby the device is placed adjacent to the tissue in association with a stabilizing device.

18. The method of claim 17 whereby the stabilizing device is selected from the group consisting of a stent, an intramedullary rod, a catheter, a balloon, and a needle.

* * * * *

(12) EX PARTE REEXAMINATION CERTIFICATE (8435th)
United States Patent
Saffran

(10) Number: US 5,653,760 C1
(45) Certificate Issued: Aug. 2, 2011

(54) METHOD AND APPARATUS FOR MANAGING MACROMOLECULAR DISTRIBUTION

(76) Inventor: Bruce N. Saffran, Brookline, MA (US)

Reexamination Request:
No. 90/009,795, Oct. 15, 2010

Reexamination Certificate for:
Patent No.: 5,653,760
Issued: Aug. 5, 1997
Appl. No.: 08/513,092
Filed: Aug. 9, 1995

Related U.S. Application Data

(63) Continuation-in-part of application No. 08/114,745, filed on Aug. 30, 1993, now Pat. No. 5,466,262.

(51) Int. Cl.
*A61B 17/68* (2006.01)
*A61F 2/02* (2006.01)
*A61F 2/00* (2006.01)

(52) U.S. Cl. ............... 623/11.11; 606/86 R; 606/154; 606/74

(58) Field of Classification Search .............. None
See application file for complete search history.

(56) References Cited

U.S. PATENT DOCUMENTS

| | | | |
|---|---|---|---|
| 3,062,210 A | 11/1962 | Scholl | |
| 3,797,485 A | 3/1974 | Urquhart | |
| 3,948,254 A | 4/1976 | Zaffaroni | |
| 3,961,628 A | 6/1976 | Arnold | |
| 3,996,934 A | 12/1976 | Zaffaroni | |
| 4,164,560 A | 8/1979 | Folkman et al. | |
| 4,186,184 A | 1/1980 | Zaffaroni | |
| 4,321,711 A | 3/1982 | Mano | |
| 4,356,166 A | 10/1982 | Peterson | |
| 4,389,330 A | 6/1983 | Tice et al. | |
| 4,391,797 A | 7/1983 | Folkman | |
| 4,447,590 A | 5/1984 | Szycher | |
| 4,464,317 A | 8/1984 | Thies et al. | |
| 4,530,840 A | 7/1985 | Tice et al. | |
| 4,542,025 A | 9/1985 | Tice et al. | |
| 4,591,496 A | 5/1986 | Cohen et al. | |
| 4,613,665 A | 9/1986 | Larm | |
| 4,622,244 A | 11/1986 | Lapka et al. | |
| 4,638,043 A | 1/1987 | Szycher | |
| 4,675,189 A | 6/1987 | Kent et al. | |
| 4,693,720 A | 9/1987 | Scharnberg | |
| 4,698,302 A | 10/1987 | Whitehead et al. | |
| 4,713,243 A | 12/1987 | Schiraldi et al. | |
| 4,733,665 A | 3/1988 | Palmaz | |
| 4,739,762 A | 4/1988 | Palmaz | |

(Continued)

FOREIGN PATENT DOCUMENTS

EP 0 335 341 A1 10/1989

(Continued)

OTHER PUBLICATIONS

Controlled Release of Biologically Active Agents, pp. 88, 89, and 160–169, 1987, Baker, John Wiley and Sons.

(Continued)

*Primary Examiner* — Jeanne M. Clark

(57) ABSTRACT

This invention is designed to help restrain small structural or minor fracture fragments (5), and the macromolecules they produce (8) in specified compartment. The device is composed of a single sheet of material (1) that in its principal embodiment is supplied as a thin, pliable, fabric that is flexible in three dimensions and is minimally porous to macromolecules. When the method of use contains the secondary step of affixing a treating material (12) to the device prior to use, additional materials can be delivered directly and preferentially into specific compartments. Moreover, because the device can be made of a soft fabric, a needle can be passed through the device and additional treating materials can be repeatedly injected into and contained after the device has been deployed. The invention also permits delivery of energy (23) directly and specifically to the treated surface. The rate of repair can be further accelerated by the attachment of a treating material (12), either mechanically or by chemical bond (24), to one surface of the device.

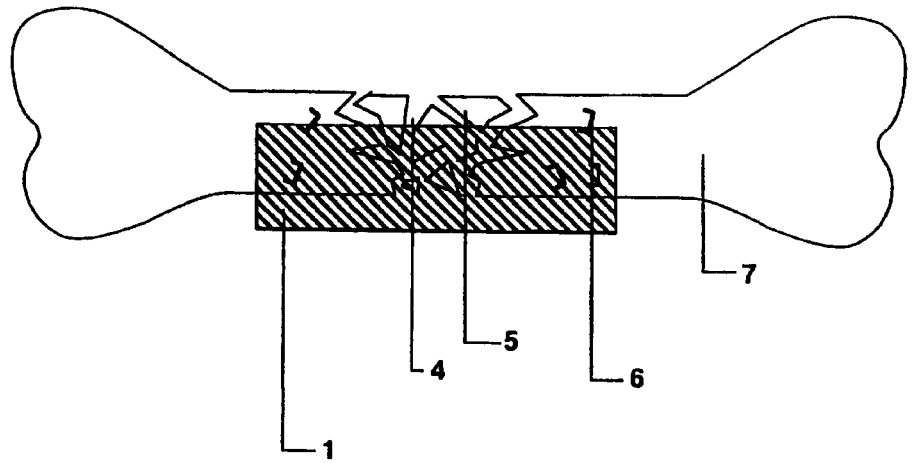

U.S. PATENT DOCUMENTS

| | | | |
|---|---|---|---|
| 4,776,337 A | 10/1988 | Palmaz | |
| 4,842,868 A | 6/1989 | Helwing | |
| 4,873,308 A | 10/1989 | Coury et al. | |
| 4,877,029 A | 10/1989 | Valentini et al. | |
| 4,879,135 A | 11/1989 | Greco et al. | |
| 4,886,062 A | 12/1989 | Wiktor | |
| 4,897,268 A | 1/1990 | Tice et al. | |
| 4,911,717 A | 3/1990 | Gaskill, III | |
| 4,931,279 A | 6/1990 | Bawa et al. | |
| 4,941,877 A | 7/1990 | Montano, Jr. | |
| 4,943,449 A | 7/1990 | Aishima et al. | |
| 5,011,486 A | 4/1991 | Aebischer et al. | |
| 5,019,096 A | 5/1991 | Fox | |
| 5,037,656 A | 8/1991 | Pitt et al. | |
| 5,041,100 A | 8/1991 | Rowland et al. | |
| 5,053,048 A | 10/1991 | Pinchuk | |
| 5,076,265 A | 12/1991 | Wokalek | |
| 5,084,051 A | 1/1992 | Tormala | |
| 5,087,244 A | 2/1992 | Wolinsky | |
| 5,102,417 A | 4/1992 | Palmaz | |
| 5,106,627 A | 4/1992 | Aebischer et al. | |
| 5,123,917 A | 6/1992 | Lee | |
| 5,152,782 A | 10/1992 | Kowligi | |
| 5,156,843 A | 10/1992 | Leong et al. | |
| 5,156,844 A | 10/1992 | Aebischer et al. | |
| 5,166,187 A | 11/1992 | Collombel et al. | |
| 5,199,951 A | 4/1993 | Spears | |
| 5,213,580 A | 5/1993 | Slepian | |
| 5,234,456 A | 8/1993 | Silvestrini | |
| 5,236,413 A | 8/1993 | Feiring | |
| 5,260,066 A | 11/1993 | Wood et al. | |
| 5,264,214 A | 11/1993 | Rhee et al. | |
| 5,282,785 A | 2/1994 | Shapland et al. | |
| 5,282,823 A | 2/1994 | Schwartz et al. | |
| 5,286,254 A | 2/1994 | Shapland | |
| 5,288,711 A | 2/1994 | Mitchell | |
| 5,290,271 A | 3/1994 | Jernberg | |
| 5,290,561 A | 3/1994 | Farhadieh et al. | |
| 5,295,962 A | 3/1994 | Crocker et al. | |
| 5,302,168 A | 4/1994 | Hess | |
| 5,304,121 A | 4/1994 | Sahatjian | |
| 5,324,775 A | 6/1994 | Rhee et al. | |
| 5,356,630 A | 10/1994 | Laurencin et al. | |
| 5,370,681 A | 12/1994 | Henveck et al. | |
| 5,383,928 A | 1/1995 | Scott et al. | |
| 5,405,919 A | 4/1995 | Keefer et al. | |
| 5,425,953 A | 6/1995 | Sintov et al. | |
| 5,447,724 A | 9/1995 | Helmus | |
| 5,449,382 A | 9/1995 | Dayton | |
| 5,457,093 A | 10/1995 | Cini et al. | |
| 5,464,450 A | 11/1995 | Buscemi et al. | |
| 5,464,650 A | 11/1995 | Berg et al. | |
| 5,466,262 A | 11/1995 | Saffran | |
| 5,466,862 A | 11/1995 | Martino | |
| 5,474,563 A | 12/1995 | Myler et al. | |
| 5,512,055 A | 4/1996 | Domb et al. | |
| 5,516,781 A | 5/1996 | Morris | |
| 5,525,357 A | 6/1996 | Keefer et al. | |
| 5,545,208 A | 8/1996 | Wolff | |
| 5,562,922 A | 10/1996 | Lambert | |
| 5,575,815 A | 11/1996 | Slepian | |
| 5,591,227 A | 1/1997 | Dinh | |
| 5,609,629 A | 3/1997 | Fearnot | |
| 5,616,608 A | 4/1997 | Kinsella | |
| 5,624,411 A | 4/1997 | Tuch | |
| 5,637,113 A | 6/1997 | Tartaglia et al. | |
| 5,650,447 A | 7/1997 | Keefer et al. | |
| 5,653,760 A | 8/1997 | Saffran | |
| 5,674,192 A | 10/1997 | Sahatjian | |
| 5,674,287 A | 10/1997 | Slepian | |
| 5,681,568 A | 10/1997 | Goldin et al. | |
| 5,716,981 A | 2/1998 | Hunter et al. | |
| 5,725,567 A | 3/1998 | Wolff | |
| 5,834,029 A | 11/1998 | Bellamkonda et al. | |
| 5,900,246 A | 5/1999 | Lambert | |
| 5,994,341 A | 11/1999 | Hunter et al. | |
| 6,120,536 A | 9/2000 | Ding et al. | |
| 6,146,358 A | 11/2000 | Rowe | |
| 6,193,746 B1 | 2/2001 | Strecker | |
| 6,436,135 B1 | 8/2002 | Goldfarb | |
| 6,545,097 B2 | 4/2003 | Pinchuk et al. | |
| 6,855,770 B2 | 2/2005 | Pinchuk et al. | |
| 7,004,976 B2 | 2/2006 | Ornberg et al. | |
| 2002/0115081 A1 | 8/2002 | Lee et al. | |
| 2004/0210289 A1 | 10/2004 | Wang et al. | |
| 2005/0152950 A1 | 7/2005 | Saffran | |
| 2006/0177476 A1 | 8/2006 | Saffran | |

FOREIGN PATENT DOCUMENTS

| | | |
|---|---|---|
| EP | 0 339 821 A1 | 11/1989 |
| EP | 0 449 592 A1 | 10/1991 |
| EP | 0 335 341 B1 | 3/1992 |
| EP | 0 551 182 A1 | 7/1993 |
| EP | 0 578 998 | 1/1994 |
| EP | 0 604 022 | 6/1994 |
| EP | 0 623 354 B1 | 9/1994 |
| JP | 2004097687 | 4/2004 |
| WO | WO 90/01969 | 3/1990 |
| WO | WO 91/12779 | 9/1991 |
| WO | WO 91/16945 | 11/1991 |
| WO | WO 91/17724 | 11/1991 |
| WO | WO 91/19529 | 12/1991 |
| WO | WO 93/06792 | 4/1993 |
| WO | WO 93/11120 | 6/1993 |
| WO | WO 94/21308 | 9/1994 |
| WO | WO 94/21309 | 9/1994 |
| WO | WO 95/03036 | 2/1995 |

OTHER PUBLICATIONS

Natural Fibers, Biopolymers, and Biocomposites, Chapter 16 (Polylactic Acid Technology), pp. 538–563, 2005, Henton, et al, CRC Press LLC.

Biodegradable porous polyurethane scaffolds for tissue repair and regeneration, J. Biomed. Mater. Research Part A, 79A:128–138, PDOI 10.1002/jbm.a.30708, 2006, Gorna, Wiley Periodicals, Inc.

Physiological Transport Forces Govern Drug Distribution for Stent–Based Delivery, Circulation, 2001; 104:600–605, 2001, Hwang, Circulation.

Blood Component Therapy, Can. Fam. Physician, vol. 30, 1809–1814, 1984, Kelton, Can. Fam. Physician.

Polymers in Transdermal Drug Delivery Systems, Pharmaceutical Technology, pp. 62–80, May 2002, Kandavilli, Pharmaceutical Technology.

Fabrication and Characterization of an Asymmetric Polyurethane Membrane for Use as a Wound Dressing, J. App. Biomaterials, vol. 3, 287–303, 1992, Hinrichs, John Wiley & Sons, Inc.

Merriam–Webster's Medical Dictionary (1995) pp. 321, 387, 394, 425, and 545.

Merriam–Webster's Collegiate Dictionary (10th ed., 1993) pp. 708, 1076, and 1292.

Merriam–Webster's Collegiate Dictionary (11th ed., 2008) pp. 624 and 966.

Stedman's Medical Dictionary (1995) pp. 857 and 1012.

Dorland's Illustrated Medical Dictionary (27th Ed. 1988) pp. 824 and 978.

Choi, J, Chen J, Schreiber, SL, and Clardy, J; "Structure of the FKBP12–Rapamycin Complex Interacting with the Binding Domain of Human FRAP"; Science; vol. 273, Jul. 12, 1996; pp. 239–242.

1994 Whitaker Lecture: Polymers for Drug Delivery and Tissue Engineering, 1995, Langer, R. Annals of Biomedical Engineering.

A New Method for Arterial Drug Delivery Via Removable Stent, Feb. 1993, Lambert et al, Journal of the American College of Cardiology.

An Explanation for the Controlled Release of Macromolecules from Polymers, 1985, Bawa, et al., Journal of Controlled Release.

Basic Fibroblast Growth Factor Release From Synthetic Guidance Channels Facilitates Peripheral Nerve Regeneration Across Long Nerve Gaps, 1989, Aebischer, P, Salessiotis, AN, and Winn, SR., Journal of Neuroscience Research.

Biocompatability of Polymeric Delivery Systems for Macromolecules, 1981, Langer, R, Brem, H and Tapper, D., Journal of Biomedical Materials Research.

Biocompatible Controlled Release Polymers for Delivery of Polypeptides and Growth Factors, 1991, Langer, R. & Moses, M., Journal of Cellular Biochemistry.

Biomaterials in Controlled Drug Delivery: New Perspectives From Biotechnological Advances, Aug. 1989, Langer, R., Pharmaceutical Tech.

Biopolymers in Controlled Release Systems, 1986, Langer, R. (Piskin, E and Hoffman, AS, eds.), Polymeric Biomaterials.

Blind–ended Semipermeable Guidance Channels Support Peripheral Nerve Regeneration in the Absence of a Distal Nerve Stump, 1988, Aebischer, P, et al., Brain Research.

Chemical and Physical Structure of Polymers as Carriers for Controlled Release of Bioactive Agents: A Review, 1983, Langer, R & Peppas, N., JMS—Rev. Macromol. Chem. Phys.

Controlled Release Delivery Systems, 1983, Roseman, TJ & Mansdorf, SZ, eds., Marcel Dekker, Inc.

Controlled Release from Polymers Containing Pesticides as Pendent Substituents, 1975, Feld, WA, Post, LK, and Harris, FW., Proceedings of 1975 International Controlled Release Pesticide Symposium.

Controlled Release of Bioactive Agents, 1984, Kost, J and Langer, R., Trends in Biotechnology.

Controlled Release of Biologically Active Agents, 1987, Baker, R., John Wiley & Sons, Inc.

Controlled Release of Macromolecules from Polymers, 1980, Langer, R & Folkman, J. (Goldberg, EP & Nakajima, A, eds.), Biomedical Polymers: Polymeric Materials and Pharmaceuticals for Biomedical Use.

Controlled Release Systems, 1988, Langer, R., Chemical Engineering Education.

Controlled Release: A New Approach to Drug Delivery., Apr. 1981, Langer, R., Technology Review.

Controlled–Release Technology: Pharmaceutical Applications, 1987, Lee, PI & Good, WR, eds.

Current Status and Potential Applications of the Harts Removable Stent, 1994, Litvack et al., Journal of Interventional Cardiology.

Current Status and Prospects For the Use of Temporary Stents, Jul. 1994, Dev et al., Coronary Artery Disease.

Design and synthesis of controlled release pesticidepolymer combinations, 1971, Allan, GG, et al., Nature.

Enzymatic Cleavage of Side Chains of Synthetic Water–Soluble Polymers, 1976, Drobnik, J, et al., Makromol. Chem.

Hydrophobic Interactions, 1980, Ben–Naim, A., Plenum Press.

Implantable Controlled Release Systems, 1983, Langer, R., Pharmac. Ther.

Implantation and Recovery of Temporary Metallic Stents In Canine Coronary Arteries, Oct. 1993, Eigler et al., Journal of the American College of Cardiology.

In vivo and in vitro Release of Macromolecules from Polymeric Drug Delivery Systems, Oct. 1983, Brown, LR, Wei, CL, and Langer, R., Journal of Pharmaceutical Sciences.

Intermolecular and Surface Forces, 2nd ed., 1992, Isrealachvili, J.N., Academic Press.

Kinetics of Drug Delivery to the Arterial Wall via Polyurethane Coated Removable Nitinol Stent—Comparative Study of 2 Drugs, 1993, Dev et al., Circulation.

Kinetics of Drug Delivery to the Arterial Wall via Polyurethane–Coated Removable Nitinol Stent: Comparative Study of Two Drugs, 1995, Dev et al., Catheterization and Cardiovascular Diagnosis.

Local Arterial Wall Drug Delivery from a Polymer Coated Removable Metallic Stent: Kinetics, Distribution and Bioactivity of Forskolin, 1994, Lambert et al., Journal of the American College of Cardiology.

Localized Arterial Drug Delivery from a Polymer Coated Removable Stent: Kinetics and Bioactivity of Forskolin, Sep. 28, 1990, Langer, Science.

Localized Arterial Wall Drug Delivery From a Polymer–Coated Removal Metallic Stent, Aug. 1994, Lambert et al., Circulation.

Localized Arterial Wall Drug Delivery From a Polymer–Coated Removable Metallic Stent: Kinetics, Distribution, and Bioactivity of Forskolin, 1993, Lambert, TL, et al., Circulation.

Long–Acting Contraceptive Delivery Systems, May 31–Jun. 3, 1983, Langer, RS. (Zatuchni, GI, et al., eds.), Proceedings of an International Workshop on Long–Acting Contraceptive Delivery Systems.

Methods for Assessing Exposure to Chemical Substances, vol. 11: Methodology for Estimating the Migratio nof Additives and Impurities from Polymeric Materials, Sep. 1992, Schwope, A.D., et al., US EPA, Office of Toxic Substances.

Methods to Achieve Controlled Drug Delivery, 1978, Chandrasekar am, SK, Benson, H, and Urquhart, J. (Robinson, JR, ed.), The Biomedical Engineering Approach in Sustained and Controlled Release Drug Delivery Systems.

New Drug Delivery Systems: What the Clinician Can Expect. Drug Therapy, Apr. 1983, Langer, R.

New Methods of Drug Delivery, Sep. 28, 1990, Langer, R. Science.

Novel Drug Delivery Systems, 2nd ed., 1992, Chien, YW.

Pesticides, pollution and polymers, Mar. 1973, Allan, GG, et al., Chemtech.

Physico–mechanical properties of degradable polymers used in medical applications: a comparative study, Apr. 1991, Engelberg, I & Kohn, J., Biomaterials.

Polyanhydrides as Drug Delivery Systems, 1990, Chasin, M, et al. (Chasin, M and Langer, R, eds.), Biodegradable Polymers as Drug Delivery Systems.

Polymeric Delivery Systems, 1990, Langer, R. (Gregoriadis, G, et al., eds.), Targeting of Drugs Plenum Press, New York.

Polymer–Controlled Drug Delivery Systems, 1993, Langer, R., Accounts of Chemical Research.

Polymeric Controlled Drug Delivery, 1987, Leong, KW and Langer R., Advanced Drug Delivery Reviews.

Polymeric Controlled Release Systems: New Methods for Drug Delivery, Jun. 1987, Laurencin, CT & Langer, R., Clinics in Laboratory Medicine.

Polymeric Controlled Release Vaccine Delivery Systems, 1996, Hanes, J and Langer, R. (Richard A Bronson, et al. eds.), Reproductive Immunology.

Polymeric Delivery Systems for Controlled Drug Release, 1980, Langer, R., Chemical Engineering Communications.

Polymeric Delivery Systems for Macromolecules: Approaches for Studying in vivo Release Kinetics and Designing Constant Rate Systems, 1982, Langer, R, Hsieh, DS, and Brown, L. (Carraher, CE & Gebelein, CG, eds.), Biological Activities of Polymers American Chemical Society.

Polymeric Drug Delivery Systems, 1980, Kim, SW, Petersen, RV, and Feijen, J. (Ariens, EJ, ed.), Drug Design.

Polymeric Drugs, 1977, Batz, H–G. (Cantow, H–J, et al., eds.), Advances in Polymer Science.

Polymeric Stents: Modern Alchemy or the Future?, May/Jun. 1991, Murphy, J.G., J. of Invasive Cardiology.

Polymers as Controlled Drug Delivery Devices for the Treatment of Malignant Brain Tumors, 1993, Brem, H, Walter KA, Langer, R., Eur. J. Pharm. Biopharm.

Polymers Containing Pendent Herbicide Substituents, 1975, Harris, FW, et al., Proceedings of 1975 International Controlled Release Pesticide Symposium.

Polymers for Biological Systems, 1996, Thompson, RC, Ishaug, SL, Mikos, AG, and Langer, R. (Meyers, RA, ed.), Encyclopedia of Molecular Biology and Molecular Medicine.

Polymers for Sustained Macromolecule Release: Procedures to Fabricate Reproducible Delivery Systems and Control Release Kinetics, Mar. 1980, Rhine, WD, Hsieh, DS, and Langer, R., J. Pharmaceutical Sciences.

Polymers for the Controlled Release of Macromolecules: Effect of Molecular Weight of Ethylene–Vinyl Acetate Copolymer, 1985, Hsu, TT and Langer, R., Journal of Biomedical Materials Research.

Polymers for the Sustained Release of Macromolecules: Controlled and Magnetically Modulated Systems, Oct. 27, 1980, Langer, RS, Hsieh, DS, Brown, L, and Rhine, W (Bearn, AG, ed.), Better Therapy with Existing Drugs: New Uses and Delivery Systems/Merck Sharp & Dohme International.

Polymers for the Sustained Release of Proteins and Other Macromolecules, Oct. 28, 1976, Langer, R & Folkman, J., Nature.

Present and Future Applications of Biomaterials in Controlled Drug Delivery Systems, Oct. 1981, Robert S. Langer & Nikolas A. Peppas, Biomaterials.

Regeneration of Transected Sciatic Nerves Through Semi–Permeable Nerve Guidance Channels, 1986, Aebischer et al., American Society for Artificial Internal Organs.

Regeneration of Transected Sciatic Nerves Through Semi–Permeable Nerve Guidance Channels: Effects of Extracellular Matrix Protein Additives, 1986, Aebischer, P, et al., Trans. Am. Soc. Artif. Intern. Organs.

Selective suppression of weeds and deciduous brush in the presence of conifers, Mar./Apr. 1972, Allan, GG, et al., International Pest Control.

Site–Specific Dexamethasone Delivery for the Prevention of Neointimal Thickening After Vascular Stent Implantation, 1994, Muller, D., et al., Coronary Artery Disease.

Studies on Norethindrone Covalently Bonded to Poly–N5–(3–Hydroxypropyl)–L–Glutamine, 1979, Peterson R. V., et al. (Division of Polymer Chemistry, Inc. American Chemical Society, ed.), Papers Presented at the Washington, D.C. Meeting.

Sustained Release of Macromolecules from Polymers, 1978, Langer, R & Folkman, J. (Kostelnik, RJ, ed.), Polymeric Delivery Systems.

Synthesis and Polymerization of the Vinyl and Acryloyloxyethyl Esters of 2,4–Dichlorophenoxyacetic Acid and 2–(2,4, 5–Trichlorophenoxy) Propionic Acid, 1975, Harris, FW & Post, LK., Polymer Letters.

Synthesis of Polymers Containing Pendent Herbicide Substituents, 1975, Harris, FW & Post, LK., Proceedings of 1975 International Controlled Release Pesticide Symposium.

Synthetic Biologically Active Polymers, 1975, Donaruma LG, Progr. Plym. Sci.

Textbook of Polymer Science, 3rd ed., 1984, Billmeyer, F. W., John Wiley & Sons.

The Role of Cytoplasmic Microtubules in Regulation of Smooth Muscle Proliferation, 1988, Katsuda et al., 8th International Symposium on Atherosclerosis.

The Role of Cytoplasmic Microtubules in Regulation of Smooth Muscle Proliferation, 1990, Katsuda et al., Clinica & Terapia Cardiovascolare.

The Use of a Semi–Permeable Tube as a Guidance Channel for a Transected Rabbit Optic Nerve, 1988, Aebischer, P, et al. (Gash, DM & Sladek, JR, eds.), Progress in Brain Research.

The $\alpha$–chymotrypsin–catalyzed hydrolysis of sepharose–bound L–phenylalanine 4–nitroanilide, Aug. 1974, Jakubke, H–D & Lange, L., FEBS Letters.

Water Transport in Polylactic Acid (PLA), PLA/Polycaprolactone Copolymers, and PLA/Polyethylene Glycol Blends, 1997, Siparsky, G.L., et al., J. of Environmental Polymer Degradation.

Wallstent.

Gianturco–Cook Z Stent.

Augusto E. Villa et al., Local Delivery of Dexamethasone for Prevention of Neointimal Proliferation in a Rat Model of Balloon Angioplasty, The Journal of Clinical Investigation, Mar. 1994, pp. 1243–1249, vol. 93, The American Society for Clinical Investigation, Inc.

Robert S. Langer & Nicholas A. Peppas, Present and future applications of biomaterials in controlled drug delivery systems, Biomaterials, Oct. 1981, pp. 201–214, vol. 2, IPC Business Press.

The Internet Stroke Center, *Pathogenesis & Pathophysiology—Arthrosclerosis and Thrombus Formation*, http://www.strokecenter.org/education/ais_pathogenesis/02_arterial_wall_injuury.htm (last visited Jun. 28, 2010).

Ward Casscells et al., *Mechanism of Restenosis*, Texas Heart Institute Journal, vol. 21, No. 1:68–77 (1994).

Excerpts of Enrique Pimentel, Hormones, Growth Factors, and Oncogenes, Ch. 6, p. 141 (2000).

Excerpt of Molecular Aspects of Placental and Fetal Membrane Autacoids, pp. 420–421 (Gregory E. Rice & Shaun P. Brennecke, eds., 1993).

Alexandre Alessi et al., *Use of rosiglitazone before and after vascular injury in hypercholesterolemic rabbits: Assessment of neointimal formation*, Thrombosis Journal, vol. 6:12, pp. 1–7 (Aug. 27, 2008).

Marc Anton, *Chapter 3—High-density Lipoproteins (HDL) or Lipovitellin Fraction*, in Bioactive Egg Compounds (Rainer Huopalahti et al. eds. 2007).

Excerpt of Polymeric Drugs and Drug Delivery Systems, p. 12 (Raphael M. Ottenbrite and Sung Wan Kim eds., 2000).

Excerpt of Surface Application of Paper Chemicals, pp. 142–155 (James Brander and Ian Thorn eds., 1997).

Excerpt of Protein Delivery: Physical Systems, pp. 48–65 (Lynda M. Sanders and R. Wayne Hendren eds., 1997).

Excerpts of Liesl K. Massey, Permeability Properties of Plastics and Elastomers (2d ed. 2003).

Excerpt of Bioadhesive Drug Delivery Systems—Fundamentals, Novel Approaches, and Development, p. 553 (Edith Mathiowitz et al., eds. 1999).

Excerpt of Silicon Based Polymers: Advances in Synthesis and Supramolecular Organization, pp. 182–183 (Francois Ganachaud et al., eds., 2008).

Excerpt of Composite Materials for Implant Applications in The Human Body, p. 19 (Russell D. Jamison & Leslie N. Gilbertson, eds., 1993).

Excerpt of 32 Photochemistry, pp. 354–355 (The Royal Society of Chemistry 2001).

James H. Hurley, *Structure, Mechanism and Regulation of Mammalian Adenylyl Cyclase*, The Journal of Biological Chemistry, vol. 274:7599–7602 (Mar. 19, 1999).

Cheng Ji et al., *Stability of pharmacokinetic studies of O-palmitoyl amylopectin anchored dipyridamole liposomes*, International Journal of Pharmaceutics, vol. 313:136–143 (2006).

Excerpt of Adenosine Receptors in Health and Disease, pp. 128–129 (Constance N. Wilson & S. Jamal Mustafa, eds.) (2009).

Ana I. Azuaga et al., *Unfolding and aggregation during the thermal denaturation of streptokinase*, European Journal of Biochemistry, vol. 269:4121–4133 (2002).

Evdokia Christova et al., *Hydrophobic Interactions in the Urokinase Active Centre*, International Journal of Peptide and Protein Research, vol. 15, No. 5:459–463 (1980).

Dow Corning Corp., *About Silicone Rubber*, http://www.dowcorning.com/content/rubber/silicone-rubber.aspx (last visited Jun. 30, 2010).

Excerpt of Joseph Kost, *Controlled Drug Delivery Systems*, in Joseph C. Salamone, Concise Polymeric Materials Encyclopedia, pp. 305–307 (1998).

Stanley G. Schultz & A.K. Solomon, *Determination of the Effective Hydrodynamic Radii of Small Molecules by Viscometry*, The Journal of General Physiology, vol. 44:1189–1199 (Jul. 1, 1961).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-11, 13 and 15-18 is confirmed.

Claims 12 and 14 were not reexamined.

* * * * *